United States Patent
Evans et al.

(10) Patent No.: US 7,413,853 B2
(45) Date of Patent: *Aug. 19, 2008

(54) MODULATION OF METABOLISM OF STEROIDS AND XENOBIOTICS

(75) Inventors: Ronald M. Evans, La Jolla, CA (US); Wen Xie, San Diego, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 392 days.

This patent is subject to a terminal disclaimer.

(21) Appl. No.: 10/482,555

(22) PCT Filed: Jul. 9, 2002

(86) PCT No.: PCT/US02/21800

§ 371 (c)(1),
(2), (4) Date: Jun. 24, 2004

(87) PCT Pub. No.: WO03/005812

PCT Pub. Date: Jan. 23, 2003

(65) Prior Publication Data

US 2004/0254135 A1 Dec. 16, 2004

Related U.S. Application Data

(60) Provisional application No. 60/304,388, filed on Jul. 9, 2001.

(51) Int. Cl.
*C12Q 1/68* (2006.01)
*C12Q 1/48* (2006.01)
*C12Q 1/34* (2006.01)
*G01N 33/53* (2006.01)

(52) U.S. Cl. .............................. 435/6; 435/7.8; 435/15; 435/18

(58) Field of Classification Search .................... 435/6, 435/7.8, 15, 18
See application file for complete search history.

(56) References Cited

U.S. PATENT DOCUMENTS

| 5,589,504 | A | 12/1996 | Dannenberg et al. |
| 6,287,834 | B1 | 9/2001 | Belanger et al. |
| 6,395,481 | B1 | 5/2002 | Di Rienzo et al. |
| 2003/0223993 | A1* | 12/2003 | Evans et al. ............... 424/144.1 |

OTHER PUBLICATIONS

Carrier et al., Isolation and characterization of the human UGT2B7 gene. Biochem Biophys Res Commun. Jun. 7, 2000;272(2):616-21.*
Wen Xie et al., Orphan nuclear receptors: the exotics of xenobiotics. J. Biol. Chem., vol. 276, Issue 41, 37739-37742, Oct. 12, 2001.*
Barwick et al., Trans-species gene transfer for analysis of glucocorticoid-inducible transcriptional activation of transiently expressed human CYP3A4 and rabbit CYP3A6 in primary cultures of adult rat and rabbit hepatocytes. Mol Pharmacol. Jul. 1996;50(1):10-6.*
Roy-Chowdhury J, et al., Nuclear receptors orchestrate detoxification pathways.Dev Cell. May 2003;4(5):607-8.*
Baes et al., A new orphan member of the nuclear hormone receptor superfamily that interacts with a subset of retinoic acid response elements, Mol. Cell Biol., 14:1544-1552, 1994.
Barwick et al., Trans-species gene transfer for analysis of glucocorticoid-inducible transcriptional activation of transiently expressed human CYP3A4 and rabbit CYP3A6 in primary cultures of adult rat and rabbit hepatocytes. *Mol. Pharmacol. 50*:10-16, 1996.
Beaune et al., Isolation and sequence determination of a cDNA clone related to human cytochrome P-450 nifedipine oxidase. *Proc. Natl. Acad. Sci. USA* 83:8064-8068, 1986.
Borcherding et al., Update on rifampin drug interactions II. *Arch. Intern. Med. 152*:711-716, 1992.
Burger et al., Paradoxical transcriptional activation of rat liver cytochrome P-450 3A1 by dexamethasone and the antiglucocorticoid pregnenolone 16$\alpha$-carbonitrile : Analysis by transient transfection into primary monolayer cultures of adult rat hepatocytes. *Proc. Natl. Acad. Sci. USA 89*:2145-2149, 1992.
Denison and Whitlock Jr., Xenobiotic-inducible transcription of cytochrome P450 genes. *J. Biol. Chem. 270*:18175-18178.
Elayadi & Corey, Application of PNA and LNA oligomers to chemotherapy. *Curr. Opin. Invest. Drugs 2*:558-561, 2001.
Fernandez-Salguero and Gonzalez, The CYP2A gene subfamily: species differences, regulation, catalytic activities and role in chemical carcinogenesis. *Pharmacogenetics 5*:S123-128, 1995.
Gonzalez et al., Pregnenolone 16α Carbonitrile-inducible P-450 gene family: Gene conversion and differential regulation. *Mol. Cell. Biol. 6*:2969-2976, 1986.

(Continued)

*Primary Examiner*—Anne Marie Wehbe
*Assistant Examiner*—Maria Leavitt
(74) *Attorney, Agent, or Firm*—Foley & Lardner LLP; Stephen E. Reiter

(57) ABSTRACT

In accordance with the present invention, there are provided methods for modulating Phase II conjugating enzymes such as, for example, UGTs. Phase II conjugating enzymes such as UGTs function in concert with Phase I monooxygenase enzymes such as cytochrome P450 enzymes (CYPs) to eliminate steroids and xenobiotics. Nuclear receptors SXR/PXR and CAR are xenosensors regulating expression of CYP genes such as CYP3A and 2B. The ability of this group of receptors to regulate expression of UGT in response to steroids and/or xenobiotics provides novel approaches for direct regulation/activation of a glucuronidation pathway, thereby providing methods to achieve physiologic homeostasis with respect to steroids and/or xenobiotics. SXR/PXR and CAR regulation/activation of UGT represents the first evidence of receptors that can transduce/transactivate both Phase I and Phase II adaptive hepatic response. In another aspect, the present invention also provides transgenic rodents expressing one or more of SXR, CAR or PXR.

4 Claims, 5 Drawing Sheets

OTHER PUBLICATIONS

Gonzalez, Human cytochromes P450 : problems and prospects. *Trends Pharmacol. Sci. 13*:346-352, 1992.

Hankinson, The Aryl hydrocarbon receptor complex. *Ann. Rev. Pharmacol. Toxicol. 35*:307-340, 1995.

Herbert et al., Pharmacokinetics and drug disposition. *Clin. Pharmacol. Ther. 52*:453-457, 1992.

Kolars et al., Identification of rifampin-inducible P450IIIA4 (CYP3A4) in human small bowel enterocytes. *J. Clin. Invest. 90*:1871-1878, 1992.

Kolars et al., CYP3A gene expression in human gut epithelium. *Pharmacogenetics 4*:247-259, 1994.

Lehmann et al., The human orphan nuclear receptor PXRis activated by compounds that regulate CYP3A4 gene expression and cause drug interactions. *J. Clin. Invest. 102*:1016-1023, 1998.

Mackenzie et al., The UDP glycosyltransferase gene superfamily : recommended nomenclature update based on evolutionary divergence. *Pharmacogenetics 7*:255-269, 1997.

Molowa et al., Complete cDNA sequence of a cytochrome P-450 inducible by glucocorticoids in human liver. *Proc. Natl. Acad. Sci. USA 83*:5311-5315, 1986.

Neuschwander-Tetri et al, Troglitazone-induced hepatic failure leading to liver transplantation. *Ann. Intern. Med. 129*:38-41, 1998.

Rendic and Di Carlo, Human Cytochrome P40 enzymes: A status report summarizing their reactions, substrates, inducers, and inhibitors. *Drug. Metab. Rev. 29*:413-580, 1997.

Schuetz and Guzelian, Induction of cytochrome P-450 by glucocorticoids in rat liver. *J. Biol. Chem. 259*:2007-2012, 1984.

Shibuya et al., An autopsy case of troglitazone-induced fulminant hepatitis. *Diabetes Care 21*:2140-2143, 1998.

Spiegelman, PPAR-y: Adipogenic regulator and thiazolidinedione receptor. *Diabetes 47*:507-514, 1998.

Tukey and Strassburg, Human UDP-Glucuronosyltransferases: Metabolism, Expression and Disease. *Annu. Rev. Pharmacol. Toxicol. 40*:581-616, 2000.

Wilson and Wahli, Peroxisome proliferators-activated receptor agonists. *Curr. Opin. Chem Biol. 1*:235-241, 1997.

Wrighton et al., Demonstration in multiple species of inducible hepatic cytochromes P-450 and their mRNAs related to the glucocorticoid-inducible cytochrome P-450 of the rat. *Mol. Pharmacol. 28*:312-321, 1985.

Xie et al., An essential role for nuclear receptors SXR/PXR in detoxification of cholestatic bile acids. PNAS, 98 : 3375-3380, 2001.

Xi et al., Humanized xenobiotic response in mice expressing nuclear receptor SXR. Natuire, 406 :435-439, 2000.

Xie et al., Reciprocal activation of xenobiotic response genes by nuclear receptors SXR/PX Rand CAR. Genes and Development, 14 :3014-3023, 2000.

International Search Report for International Application No. PCT/US02/21800.

* cited by examiner

MODULATION OF METABOLISM OF STEROIDS AND XENOBIOTICS

RELATED APPLICATIONS

This application claims the benefit of U.S. Provisional Application No. 60/304,388 filed Jul. 9, 2001, the contents of which are hereby incorporated by reference herein in their entirety.

FIELD OF THE INVENTION

The present invention relates to intracellular receptors, nucleic acids encoding same, and uses therefor. In a particular aspect, the present invention relates to methods for the modulation of physiological response to steroids and/or xenobiotic compounds.

BACKGROUND OF THE INVENTION

Nuclear receptors constitute a large superfamily of ligand-dependent and sequence-specific transcription factors. Members of this family influence transcription either directly, through specific binding to the promoters of target genes (see Evans, *Science* 240:889-895, 1988), or indirectly, via protein-protein interactions with other transcription factors (see, for example, Jonat et al., *Cell* 62:1189-1204, 1990; Schule et al., *Cell* 62:1217-1226, 1990; and Yang-Yen et al., *Cell* 62:1205-1215, 1990). The nuclear receptor superfamily (also known in the art as the "steroid/thyroid hormone receptor superfamily") includes receptors for a variety of hydrophobic ligands, including cortisol, aldosterone, estrogen, progesterone, testosterone, vitamin $D_3$, thyroid hormone and retinoic acid, as well as a number of receptor-like molecules, termed "orphan receptors" for which the ligands remain unknown (see Evans, supra). These receptors all share a common structure indicative of divergence from an ancestral archetype.

Lipophilic hormones such as steroids, retinoic acid, thyroid hormone, and vitamin $D_3$ control broad aspects of animal growth, development, and adult organ physiology. The effects of these hormones are mediated by a large superfamily of intracellular receptors that function as ligand-dependent and sequence-specific transcription factors. The non-steroidal nuclear receptors for thyroid hormone (TR), vitamin $D_3$ (VDR), all-trans retinoic acid (RAR), and fatty acids and eicosanoids (PPAR) form heterodimers with the 9-cis retinoic acid receptor (RXR) that bind bipartite hormone-response elements (HREs) composed of directly repeated half sites related to the sequence AGGTCA (Mangelsdorf and Evans, *Cell* 83: 841-850, 1995). In contrast, the steroid receptors function as homodimers and bind to palindromic target sequences spaced by three nucleotides (Beato et al., *Cell* 83: 851-857, 1995). In addition to the known receptors, a large group of structurally-related "orphan" nuclear receptors has been described which possess obvious DNA and ligand binding domains, but lack identified ligands (Mangelsdorf et al., *Cell* 83:835-839, 1995; Enmark and Gustafsson, *Mol. Endocrinol.* 10:1293-1307, 1996; and O'Malley and Conneely, *Mol. Endocrinol.* 6:1359-1361, 1992). Each has the potential to regulate a distinct endocrine signaling pathway.

It is widely viewed that the hormone response is a consequence of the release, from an endocrine gland, of a ligand that circulates through the blood, and coordinately regulates responses in target tissues by acting through specific nuclear receptors. Hormone responsiveness is dependent on the ability to rapidly clear ligand from the blood and the body so that, in absence of a stimulus, target tissues return to a ground state. Hormonal homeostasis is thus achieved by the coordinated release and degradation of bioactive hormones. Steroid hormones and their many metabolites are primarily inactivated by reduction and oxidation in the liver. Since hundreds of adrenal steroids have been identified (e.g., dozens of each of the sex steroids (androgens, estrogens and progestins), 25-35 vitamin D metabolites, and likely hundreds of fatty acids, eicosanoids, hydroxyfats and related bioactive lipids), the problem of efficient ligand elimination is critical to physiologic homeostasis. In addition to the existence of a myriad of endogenous hormones, a similar diversity of ingested plant and animal steroids and bioactive xenobiotic compounds must also be degraded. Such compounds often are lipophilic and may accumulate to toxic levels unless they are metabolized to water-soluble products that can be readily excreted. Therefore, the efficient detoxification of harmful xenobiotics is essential to the survival of all organisms.

Selye first introduced the concept that exogenous steroids and pharmacological substances may function to modulate the expression of enzymes that would protect against subsequent exposure to toxic xenobiotic substances (Selye, *J. Pharm. Sci.* 60:1-28, 1971). These compounds, which Selye called "catatoxic steroids", are typified by the synthetic glucocorticoid antagonist, pregnenolone-16-carbonitrile (PCN). PCN, and a variety of xenobiotic steroids, induce the proliferation of hepatic endoplasmic reticulum and the expression of cytochrome P450 genes (Burger et al., *Proc. Natl. Acad. Sci. USA* 89:2145-2149, 1992; Gonzalez et al., *Mol. Cell. Biol.* 6:2969-2976, 1986; and Schuetz and Guzelian, *J. Biol. Chem.* 259:2007-2012, 1984).

Cytochrome P450 (CYP) enzyme(s), present in the endoplasmic reticulum of livers, often catalyze the initial step in the above-described detoxification pathways in what can be considered Phase I of the hepato-gastrointestinal tract steroids and/or xenobiotics modification/clearance pathway. P450s are crucial for the detoxification of most xenobiotics, including various environmental pollutants, procarcinogens, and drugs (for review, see Denison and Whitlock Jr., *J. Biol. Chem.* 270:18175-18178, 1995). In addition, CYPs are also responsible for the reduction and oxidation of steroid hormones and their many metabolites.

The Phase II hepato-gastrointestinal tract steroids and/or xenobiotics modification and/or clearance pathway comprises enzymes such as UDP-glucuronosyl transferases (UGTs), sulfotransferases (STs), glutathione-S-transferases (GSTs), and N-acetyltransferases (NAT). These conjugating enzymes add bulky, water-soluble substances to target substrates and facilitate the partition of these metabolites from the lipid into the aqueous compartments and subsequent elimination from the vertebrate body. The combined functions of the Phase II reactions assure that many endogenously generated catabolic products as well as xenobiotic agents are efficiently removed through excretion to the bile or urine.

UGTs are expressed in the hepato-gastrointestinal tract including, for example, the liver, biliary tract, stomach, duodenum, and colon. Up to 16 UGT gene products have been identified in humans. Based upon amino acid sequence relatedness and evolutionary divergence, these proteins have been classified into families, such as UGT1 and UGT2 (Mackenzie et al., *Pharmacogenetics* 7:255-269, 1997). Using UDP-glucuronic acid (UDPG1cUA) as a cosubstrate, UGTs add glucuronic acid to a variety of target substances and thus convert small lipophilic molecules to water-soluble glucuronides. The UGTs have a wide spectrum of substrates including more than 350 known agents such as steroids, heme byproducts, free fatty acids, environmental contaminants, xenobiotics, drugs, and dietary byproducts (Tukey and Strassburg, *Annu. Rev. Pharmacol. Toxicol.* 40:581-616, 2000). This large classification of substrates spans many structurally divergent chemical classes such as alcohols, flavones, coumarins, carboxylic acids, amines, opioids, and steroids. Since glucuronides rarely retain biological activity, the glucuronidation is regarded as a "detoxification" mechanism (Dutton, *Biochem. Pharmacol.* 24:1835-1841, 1975).

Biochemical and genetic studies similar to studies which illustrate that SXR/PXR can regulate CYP3A genes, were performed for CAR. The studies establish that CAR is a CYP2B regulator through the phenobarbital-responsive element (PBRE) found in the promoters of inducible CYP2B genes. The PBRE contains two imperfect DR-4 type of nuclear receptor (NR) binding sites.

One consequence of treatment with a catatoxic steroid such as PCN is the induction of nonspecific "protection" against subsequent exposure to such diverse xenobiotics as digitoxin, indomethacin, barbiturates, and steroids (Selye, supra). Furthermore, it is known that a variety of such compounds can activate P450 genes responsible for their detoxification or degradation (Fernandez-Salguero and Gonzalez, *Pharmacogenetics* 5:S123-128, 1995; Denison and Whitlock Jr., supra; Hankinson, *Ann. Rev. Pharmacol. Toxicol.* 35:307-340, 1995; and Rendic and Di Carlo, *Drug Metab. Rev.* 29:413-580, 1997). P450s constitute a superfamily; each form possesses an overlapping but distinct substrate specificity. Some P450 genes are expressed constitutively, while others, particularly those involved in xenobiotic metabolism, are inducible. In many cases, inducers are also substrates for the induced enzymes, therefore, P450 activities typically remain elevated only as needed. Among the CYP gene family members, the CYP3A isoenzyme is of particular significance from a medical perspective. The human CYP3A4 enzyme is involved in the metabolism of a large number of clinical drugs including antibiotics, antimycotics, glucocorticoids, and the statin class of HMG-CoA reductase inhibitor (Maurel, *Ioannides C Ed*. (CRC Press, Boca Raton, Fla.). pp. 241-270, 1996). Indeed, the drug-induced CYP3A4 activation constitutes the molecular basis for a number of important clinically known drug interactions. CYP3A23 and CYP3A11 are rodent homologues of CYP3A4 in rat and mouse, respectively. Indeed, purified CYP3A11 (P450MDX-B) exhibited comparable activity to CYP3A1 (another rat CYP3A homologue, Halvorson et al., *Arch.Biochem. Biophys.* 277:166-180, 1990) and CYP3A4 (Yamazaki and Shimada, *Arch. Biochem. Biophys.* 346:161-169, 1997) for testosterone 6β-hydroxylation, which is thought to be one of specific reactions for the CYP3A enzyme in rodents and primates (Matsunaga et al., *Drug. Metab. Dispos.* 26:1045-1047, 1998). The regions of the 5' regulatory sequences of CYP3A23 and CYP3A11 share high homology, including multiple putative response elements (Toide et al., *Arch. Biochem. Biophy.* 338:43-49, 1997), indicating similar transcriptional regulatory mechanisms among these rodent CYP3A genes.

Although there are substantial structural and catalytic similarities among the various members of the CYP3A family across species lines, important differences exist in regulatory control of these genes (for review, see Gonzalez, *Pharmacol. Ther.* 45:1-38, 1990; and Nelson, *Arch. Biochem. Biophys.*, 369:1-10, 1999). For example, a clear discrepancy between human and rodents is that the antibiotic RIF induces CYP3A4 in human liver (Watkins and Whitcomb, *N. Engl. J. Med.* 338:916-917, 1998) but does not induce CYP3A23 in rats (Wrighton et al., *Mol. Pharmacol.* 28:312-321, 1985) and CYP3A11 in mice (Schuetz et al., *Proc. Natl. Acad Sci. USA* 93:4001-4005, 1996), respectively. On the other hand, the anti-glucocorticoid PCN, which induces CYP3A23 in rat liver (Wrighton et al., supra), only weakly induces human CYP3A4 (Schuetz et al., *Hepatology* 18:1254-1262, 1993; Kocarek et al., *Drug Metab. Dispos.* 23:415-421, 1995; Blumberg and Evans, *Genes Dev.* 12:3149-3155, 1998), and does not induce CYP3A6 (Dalet et al., *DNA* 7: 39-46, 1988), a rabbit homolog with a drug response specificity similar to CYP3A4 (Barwick et al., *Mol. Pharmacol.* 50: 10-16, 1996). Given the widespread metabolic importance of CYP3A, it would be of great clinical benefit to find an appropriate animal model for use in developing a better understanding of the regulatory control and inter-individual heterogeneity in liver expression of CYP3A in humans.

While it appears that catatoxic compounds such as PCN regulate the expression of cytochrome P450s and other detoxifying enzymes, two lines of evidence argue that such regulation is independent of the classical steroid receptors. First, many of the most potent compounds (e.g., PCN, spironolactone, and cyproterone acetate) have been shown to be steroid receptor antagonists; whereas others (e.g., dexamethasone) are steroid receptor agonists (Burger, supra). Second, the nonspecific protective response remains after bilateral adrenalectomy (and presumably in the absence of adrenal steroids), but not after partial hepatectomy (Selye, supra).

Insight into the mechanism by which PCN exerts its catatoxic effects is provided by the demonstration that PCN induces the expression of CYP3A1 and CYP3A2, two closely related members of the P450 family of monooxygenases (see, for example, Elshourbagy and Guzelian, *J. Biol. Chem.* 255: 1279-1285, 1980; Heuman et al., *Mol. Pharmacol.* 21:753-760, 1982; Hardwick et al., *J. Biol. Chem.* 258:8081-8085, 1983; Schuetz and Guzelian, supra; Schuetz et al., *J. Biol. Chem.* 259:1999-2006, 1984; and Gonzalez et al., *J. Biol. Chem.* 260:7435-7441, 1985). The CYP3A hemoproteins display broad substrate specificity, hydroxylating a variety of xenobiotics (e.g., cyclosporin, warfarin and erythromycin), as well as endogenous steroids (e.g., cortisol, progesterone, testosterone and DHEA-sulfate. See, for example, Nebert and Gonzalez, *Ann. Rev. Biochem.* 56:945-993, 1987 and Juchau, *Life Sci.* 47:2385-2394, 1990). A PCN response element (which is highly conserved in the CYP3A2 gene promoter) has since been identified in subsequent studies with the cloned CYP3A1 gene promoter (see Miyata et al., *Arch. Biochem. Biophys.* 318:71-79, 1995 and Quattrochi et al., *J. Biol. Chem.* 270:28917-28923, 1995). This response element comprises a direct repeat of two copies of the nuclear receptor half-site consensus sequence AGTTCA.

In addition to inducing CYP3A gene expression, PCN has also been shown to have marked effects on hepatic cholesterol homeostasis. These effects include significant decreases in the levels of HMG-CoA reductase and cholesterol 7a-hydroxylase gene expression, with associated reductions in sterol biosynthesis and bile acid secretion. PCN has also been reported to enhance the formation of cholesterol esters and the hypersecretion of cholesterol into the bile. Thus, PCN affects key aspects of cholesterol metabolism, including its biosynthesis, storage and secretion.

Activation of orphan nuclear receptor(s) by catatoxic steroids provides a possible mechanism for the induction of xenobiotic metabolizing enzymes by compounds that do not activate known steroid receptors. Because such enzymes are activated by high (pharmacological) doses of xenobiotic and natural steroids, such a "sensor" would be expected to be a broad-specificity, low-affinity receptor. Such receptors could be activated not only by endogenous steroids and metabolites but also by exogenous compounds such as phytosteroids, xenobiotics and pharmacological inducers. Indeed, it is known that a variety of such compounds can activate P450 genes responsible for their detoxification or degradation (see, for example, Fernandez-Salguero and Gonzalez, supra; Denison and Whitlock, Jr., supra; Hankinson, supra; and Rendic and Di Carlo, supra).

In healthy individuals, steroid levels are tightly regulated, with increased catabolism of endogenous steroids being compensated by the pituitary releasing an increase of ACTH, which stimulates biosynthesis, and maintenance of plasma steroid levels. The increased catabolism is reflected by elevated urinary levels of steroid metabolites. Indeed, it is already known that treatment with rifampicin increases urinary metabolites, such as 6β-hydroxycortisol (Ohnhaus et al., Eur. J. Clin. Pharmacol. 36:39-46, 1989; and Watkins et al., J. Clin. Invest. 83:688-697, 1989), and bile acid metabolites, such as 6β-hydroxy hyocholic and 6α-hyodeoxycholic acids (Wietholtz et al., J. Hepatol, 24:713-718, 1996), while the plasma levels of many circulating steroids rise slightly due to increased synthesis (Lonning et al., J. Steroid Biochem. 33:631-635, 1989; Bammel et al., Eur. J. Clin. Pharmacol. 42:641-644, 1992; and Edwards et al., Lancet 2:548-551, 1974).

When synthetic steroids, such as prednisolone (McAllister et al., Br. Med. J. 286:923-925, 1983; and Lee et al., Eur. J. Clin. Pharmacol. 45:287-289, 1993) or 17α-ethynylestradiol (Guengerich, Life Sci. 47:1981-1988, 1990) are administered together with rifampicin, plasma levels are rapidly decreased due to enhanced urinary clearance. In some patients undergoing rifampicin therapy for tuberculosis, the increase in urinary steroid levels has led to misdiagnosis of Cushing's syndrome (Kyriazopoulou and Vagenakis, J. Clin. Endocrinol. Metab. 75:315-317, 1992; Zawawi et al., Ir. J. Med. Sci. 165:300-302, 1996; and Terzolo et al., Horm. Metab. Res. 27:148-150, 1995). In these patients, steroid production and clearance normalized when rifampicin was withdrawn. In patients with Addison's disease, who mostly lack the ability to synthesize adrenal steroids, rifampicin treatment leads to rapid depletion of endogenous and administered steroids. These documented clinical situations confirm that induction of CYP3A4 causes increased steroid catabolism (Kyriazopoulou et al., J. Clin. Endocrinol. Metab. 59:1204-1206, 1984; and Edwards, supra). However, the art is silent regarding the mechanism by which steroid metabolism is regulated in the body.

Although therapeutically administered steroids are beneficial in achieving therapeutic goals, such compounds can, in some cases, increase the overall level of steroids and xenobiotics above physiologically compatible levels in the subjects to whom they are administered. In other cases, the increased level of steroids and/or xenobiotics may linger in the body longer than is therapeutically required. In addition, some subjects are treated with combinations of steroids and xenobiotics that may be administered separately to treat different conditions, but which, in combination, have an additive, or even synergistic, effect known as a drug interaction. In such cases, the patient may be unaware when a physiologically incompatible level of steroids and xenobiotics has been reached, or when an otherwise therapeutic amount of a steroid becomes potentially dangerous due to combined effects of separately administered drugs.

For example, thiazolidinediones (TZDs) are a new class of oral antidiabetic agents, and have been identified to be synthetic ligands for peroxisome proliferator-activated gamma (PPARδ) (for reviews, see Spiegelman, Diabetes 47:507-514, 1998, and Wilson and Wahli, Curr. Opin. Chem Biol. 1:235-241, 1997). Troglitazone is the first TZD introduced for clinical use. Although troglitazone is effective in reducing hyperglycemia, concern has been raised by several reports of severe hepatic dysfunction leading to hepatic failure in patients receiving the drug (Neuschwander-Tetri et al, Ann. Intern. Med. 129:38-41, 1998, Shibuya et al., Diabetes Care 21:2140-2143; 1998, and for a review, see Watkins and Whitcomb, 1998). The mechanism of the liver toxicity by TZDs remains largely unknown.

Accordingly, there is still a need in the art for methods for mediation of the physiological effect(s) of steroids and xenobiotics, particularly when combinations of such compounds disrupt homeostasis or cause drug interaction.

SUMMARY OF THE INVENTION

The present invention provides methods for modulating Phase II conjugating enzymes such as, for example, UDP-glucuronosyltransferases(UGTs). The invention also provides methods of evaluating toxicity of a compound using transgenic rodents expressing one or more of SXR, CAR or PXR.

Phase II conjugating enzymes such as UGTs function in concert with Phase I monooxygenase enzymes such as the cytochrome P450 enzymes (CYPs) to eliminate steroid hormones and xenochemicals. Xenobiotic nuclear receptors, such as, for example, steroid xenobiotic receptor (SXR/PXR) and constitutively active receptor (CAR) (Baes et al., Mol. Cell Bio., 14:1544-1552, 1994), are xenosensors that regulate the expression of CYP genes such as CYP3A and 2B genes. In accordance with the present invention it has been discovered that xenobiotic nuclear receptors, e.g., SXR/PXR and CAR, are also involved in activating a family of UGTs, to glucuronidate a variety of xenobiotics and endogenous compounds leading to their elimination.

Accordingly, the present invention provides methods for modulating the metabolism of one or more steroid and/or xenobiotic compound(s) in a subject in need thereof, said method comprising administering to the subject an effective amount of a modulator of UGT.

In accordance with another aspect of the present invention, there are provided methods for preventing steroid toxicity in a subject undergoing treatment of a disease state involving therapeutic administration of one or more steroid compounds. This method comprises promoting UGT glucuronidation of steroids and xenobiotics.

In accordance with yet another aspect of the present invention, there are provided assays for determining whether one or more test compound(s) activate UGT glucuronidation. These invention assays comprise contacting a host cell containing a xenobiotic nuclear receptor polypeptide and a reporter construct under control of a UGT response element with one or more test compound(s) in an appropriate culture medium, and determining whether test compound(s) promote(s) expression of the reporter.

In accordance with a further aspect of the present invention, there are provided methods of screening for drugs with reduced drug-drug interaction potential. These methods comprise administering one or more test compound(s) to a transgenic rodent and screening the hepato-gastrointestinal tissues and/or fluids thereof to ascertain glucuronidation levels, wherein said transgenic rodent comprises one or more transgenes encoding a xenobiotic nuclear receptor.

In accordance with another aspect of the present invention, there are provided methods for evaluating the pharmacokinetics of a test compound. These methods comprise measuring clearance and/or glucuronidation of a test compound when administered to a transgenic mouse having at least one exogenous xenobiotic nuclear receptor transgene, wherein the native xenobiotic nuclear receptor of said mouse has been inactivated.

In accordance with yet another aspect of the present invention, there are provided transgenic mice comprising a UGT gene as part of the genome or as part of an extragenomic vector and at least one exogenous xenobiotic nuclear receptor transgene, wherein the native xenobiotic nuclear receptor of said mouse has been inactivated. Such mice can be used to measure the toxicity of a test compound according to further invention methods. Such mice can also be used to determine the therapeutic index of a test compound, by comparing the dose of test compound which is detrimental to the health of said mouse to the dose of test compound which is sufficient to activate UGT gene expression.

In accordance with another aspect of the present invention, there are provided further methods for evaluating the toxicity of a test compound. These methods comprise measuring the toxicity of a test compound to mammalian cells comprising a UGT gene as part of the genome or as part of an extragenomic vector, said cells further comprising at least one exogenous xenobiotic nuclear receptor transgene.

In accordance with another aspect of the present invention, there are provided probes comprising single-stranded nucleic acid, comprising at least 20 contiguous bases in length having substantially the same sequence as any 20 or more contiguous bases selected from bases of UGT DNA or mRNA sequences, or the complement thereof.

In accordance with another aspect of the present invention, there are provided methods to assess the tissue sensitivity of an individual to exposure to steroid and steroid-like compounds. These methods comprise determining UGT mRNA levels in a given tissue sample from said subject, wherein elevated UGT levels, relative to normal, are indicative of enhanced sensitivity.

In accordance with another aspect of the present invention, there are provided methods for rapidly screening compounds to determine which compounds are putative agonists and/or antagonists of xenobiotic nuclear receptor polypeptides and methods for identifying new ligands for UGT. These methods comprise determining whether test compounds promote binding to UGT inverted repeats and/or direct repeats.

In accordance with another aspect of the present invention, there are provided methods to determine the glucuronidation levels or absence of glucuronidation of xenobiotics. These methods comprise comparing the water solubility of xenobiotics obtained from biological samples to the water solubility of non-glucuronidated xenobiotics.

In accordance with yet another aspect of the present invention, there are provided methods for inducing the expression of steroid degradative enzymes. These methods comprise activating SXR/PXR and/or CAR.

BRIEF DESCRIPTION OF THE FIGURES

FIG. 3A shows the constitutive up-regulation of hepatic UGT mRNA in transgenic rodents mice) expressing SXR.

FIG. 3B shows the lack of up-regulation of intestinal UGT mRNA in transgenic rodents (mice) expressing SXR.

FIGS. 3C and 3D show the activation of UGT by RIF in transgenic rodents (mice) but not in wild-type mice.

FIG. 4 collectively shows the glucuronidation of different substrates.

DETAILED DESCRIPTION OF THE INVENTION

Figure 1:
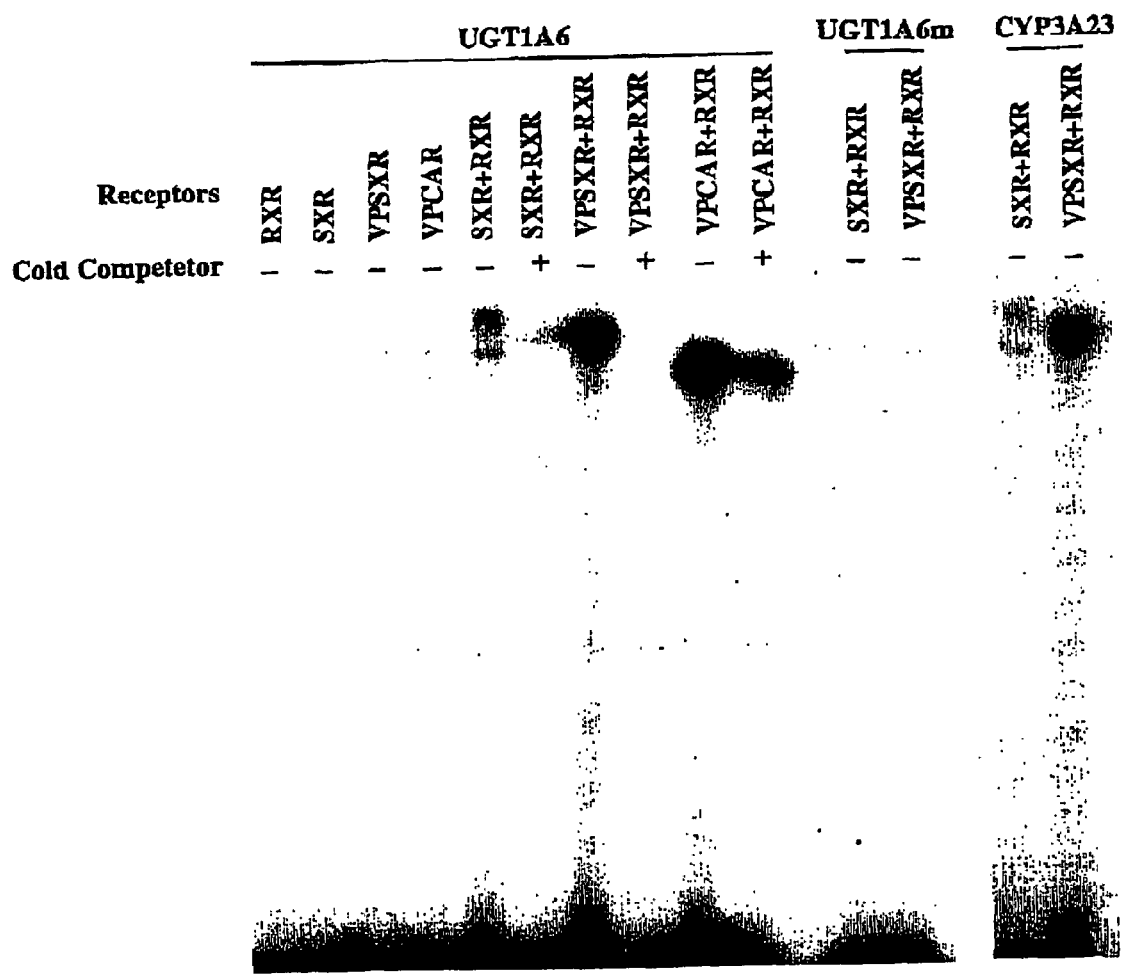
FIG. 1 shows the results of electromobility shift assays (EMSA) of SXR:RXR and CAR:RXR heterodimers bound to UGT1A6/DR-3. SXR and CAR bind to UGT1A6 through the DR-3 response element. Also provided are nucleic acid sequences (SEQ ID NOS 18, 34 and 16, respectively in order of appearance) of the DR-3 NR response element derived from the UGT1A6 gene. A mutant variant of the DR-3 (UGT1A6m, with mutated nucleotides underlined) as well as a DR-3 type SXR/PXR response element found in the rodent (rat) CYP3A23 gene are also provided.

In accordance with an aspect of the present invention, methods are provided for modulating the metabolism or clearance of one or more steroid and/or xenobiotic compound(s) in a subject in need thereof. The method includes administering to the subject an effective amount of a modulator of UGT. Following such administration, UGT is activated and causes an up-regulation of glucuronidation of steroids and/or xenobiotic compounds and thereby upregulates clearance of the same. In a particular embodiment of this aspect, a modulator of UGT that activates UGT glucuronidation of steroids and/or xenobiotic compounds is administered to a subject directly, bypassing modulation of SXR/PXR and/or CAR. Preferably, the modulator can be a xenobiotic compound, a nucleic acid and/or protein which activates a xenobiotic nuclear receptor, or a nucleic acid, protein and/or chemical compound which binds an a direct repeat or inverted repeat. More preferably, the modulator activates UGT glucuronidation of xenobiotic compounds and/or steroids.

As used herein, "administering" refers to the introduction into the subject of a compound systemically or locally. Techniques for administration may be found in "Remington's Pharmaceutical Sciences", 1990, 18$^{th}$ ed., Mack Publishing Co., Easton, Pa. Suitable routes for administration may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

As used herein, UGT is activated" refers to any action that results in the increase in UGT activity. For example, such increase can be achieved by an increase in transcription or translation of a UGT nucleic acid, an increase in stability of UGT nucleic acid or protein, an increase in protein activity, and the like.

As used herein the terms "clearance" or "clear" refer to the removal of steroids and/or xenobiotic compounds from the body of a subject. Clearance mechanisms include biological pathways of the hepato-gastrointestinal tract which includes both cells and tissues of the liver, biliary tract, stomach, duodenum, colon, and the like. Clearance can be assessed at the cellular, tissue, organ and organism levels. A steroid and/or xenobiotic compound can be considered "cleared" when the compound is removed from the cell, tissue, organ or organism of interest, or converted or modified to a different chemical form, e.g., a derivative compound. The term "xenobiotic" as used herein refers to any biologically active substance that is not endogenously produced, and, is therefore foreign to an organism. The term "steroid" as used herein refers to the entire class of compounds as is known to one skilled in the art, including both natural and synthetic chemical substances comprising a tetracyclic cyclopenta[α] phenanthrene skeleton.

As used herein the term modulating" refers to an alteration in the rate or efficiency of metabolism. Modulation may result in an increase or decrease in metabolism.

As used herein, "modulator of UGT" refers to a compound that results in an increase or decrease in UGT activity. For example, such increase or decrease can be achieved by altering the transcription or translation of a UGT nucleic acid, an alteration in stability of UGT nucleic acid or protein, an alteration in protein activity, and the like.

The term "nucleic acid" or "polynucleotide" as used herein denotes a polymer, typically linear, that contains any number of component nucleotides, usually linked from one ribose (or deoxyribose) moiety to another via phosphoric residues. A polynucleotide may be natural or synthetic, and may be single-stranded or double-stranded. Accordingly, this category that includes deoxyribonucleotides (DNA) and ribonucleotides (RNA), in which uracil (U) is present in place of thymidine (T), as well as alternative forms of either type of nucleotide, such as genomic DNA (gDNA), complementary DNA (cDNA), messenger RNA (mRNA), and transfer RNA (tRNA). A polynucleotide also includes non-traditional nucleic acids with altered backbone structures, such as peptide nucleic acid (PNA) and locked nucleic acid (LNA) oligomers (for example, see Elayadi & Corey, *Curr. Opin. Invest. Drugs* 2:558-561, 2001).

The term "protein" or "polypeptide" or "peptide" as used herein denotes a chain of amino acids, regardless of length or post-translational modification (e.g., glycosylation, phosphorylation, or attachment of lipid). A polypeptide, protein or peptide is essentially a polymer in which the monomers are amino acid residues that are joined together through amide bonds. The polypeptide or peptide of the invention may be naturally occurring, as well as those that are recombinantly or synthetically synthesized. Polypeptide or peptide fragments are also encompassed by the invention.

In another aspect of the invention, methods are provided for preventing steroid toxicity in a subject undergoing treatment of a disease state involving therapeutic administration of one or more steroid compounds. These invention methods comprise promoting UGT glucuronidation of steroids and xenobiotics. In preferred embodiments, such methods comprise administering to such a patient an effective amount of one or more ligands for a xenobiotic nuclear receptor; or a xenobiotic receptor polypeptide; or a vector containing a xenobiotic nuclear receptor operably linked to an inducible promoter. In a particular embodiment of this invention, a polypeptide and/or nucleic acid fragment is administered, wherein the polypeptide and/or nucleic acid fragment binds a UGT response element.

The term "toxicity" as used herein, refers to the possible adverse effect of administration to a subject of one or more compounds. Adverse effects can be assessed at the subcellular, cellular, tissue, organ and organism levels. When the compound is a drug administered to diagnose, prevent or treat a preexisting condition or disease, adverse effects such as side effects may result.

Steroid toxicity can result from a variety of causes, dietary build-up (of for example, estrogens), from drug overdose, reduced clearance of steroid, administration of steroid for therapeutic purpose, from a drug interaction between therapeutically administered compounds, or between one or more endogenous steroids and one or more dietary and/or therapeutically administered compounds, and the like. Commonly administered therapeutic drugs that tend to accumulate or cause a drug interaction in certain individuals leading to an increase in the overall level of steroid and xenobiotics above a physiologically suitable level include tamoxifen, ralozifene (e.g., in treatment of breast cancer), vitamin K (e.g., in treatment of osteoporosis), calcium channel blockers, such as nifedipine, and the like.

For example, rifampin (i.e., rifampicin), or an active derivative or analog thereof, is commonly used to treat tuberculosis. Yet rifampin can cause hepatic clearance of other therapeutic drugs, such as oral contraceptives (which may result in unwanted pregnancy), warfarin (which may result in decreased prothrombin times), cyclosporine and prednisone (which may result in organ rejection or exacerbations of any underlying inflammatory condition), and verapamil and diltiazem (which may result in increased dosage requirements). Similarly, treatment of osteoporosis with the therapeutic steroid Vitamin K can result in altered levels of other therapeutic compounds.

As used herein the term "preventing" refers to inhibiting, reducing or eliminating the symptoms or adverse effects.

As used herein "disease state" refers to any deviation from or interruption of the normal structure or function of any part, organ, or system (or combinations) of the body that is manifested by a characteristic set of symptoms and signs and whose etiology, pathology, and prognosis may be known or unknown. Dorland's Illustrated Medical Dictionary, (W. B. Saunders Co. 27th ed. 1988)

As used herein "therapeutic" refers to treatment or prevention of the development of a disease state.

The term "glucuronidation" as used herein refers to the enzymatic modification of target molecules to obtain bulky, water-soluble moieties. This process can facilitate partitioning of the conjugated molecules into aqueous physiological compartments for elimination. As used herein, "UGT glucuronidation" refers to UDP-glucuronosyltransferases (UGTs) that catalyze the glucuronidation of steroids and/or xenobiotics.

In yet another aspect, the invention provides assays for determining whether a test compound, or a combination thereof, will activate UGT glucuronidation. The assay comprises contacting a host cell containing a xenobiotic nuclear receptor polypeptide and a reporter construct under control of a UGT response element, with one or more test compound(s) in an appropriate culture medium. The invention assay further comprises determining whether the administered test compound promotes expression of the reporter.

It has been discovered that compound(s) that will activate transcription of the DNA contained in the above-described reporter vector are agonists of the SXR/PXR and/or CAR receptor and fall into the category of "steroids and/or xenobiotics" as the term is used herein.

It has further been discovered that compounds determined by the above assay to activate transcription of the DNA contained in the above described reporter vector are likely to become involved in a drug interaction if administered to a subject at a therapeutic level. The phrase "drug interaction" as used herein refers to the pharmacological result of a combination of two or more compounds. Compounds include steroids and/or xenobiotics, whether such compounds are endogenously produced, result from dietary sources, or are therapeutically administered to a subject in treatment of a particular disease state. For example, administration of one drug that alters a beneficial effect of a second drug is a drug interaction. Certain drug interactions are undesirable, such as when administration of one drug reduces the beneficial effects of a second drug that is administered for therapeutic, preventive or diagnostic purpose.

More particularly, there is a greater than 30% likelihood, for example a likelihood of about 45% to about 90%, or from about 50% to about 70%, that a therapeutic dose of such a compound will cause a drug interaction as described herein, with other. Therefore, in one particular aspect, the invention assay is a method for screening compounds, particularly potential therapeutic compounds, to determine those with at least a 30% likelihood of becoming involved in an undesirable drug interaction if administered to a subject at a therapeutic level. Such a screening assay is a valuable adjunct to any drug development program because it will identify those drug candidates that must be thoroughly screened in vivo to determine their safety, thereby reducing the cost of drug development in general while preventing the possibility that a drug candidate will prove potentially dangerous due to its capacity to cause unhealthy elevation of steroid levels or too rapid clearance of another therapeutically administered compound due to a "drug interaction."

Figure 2:
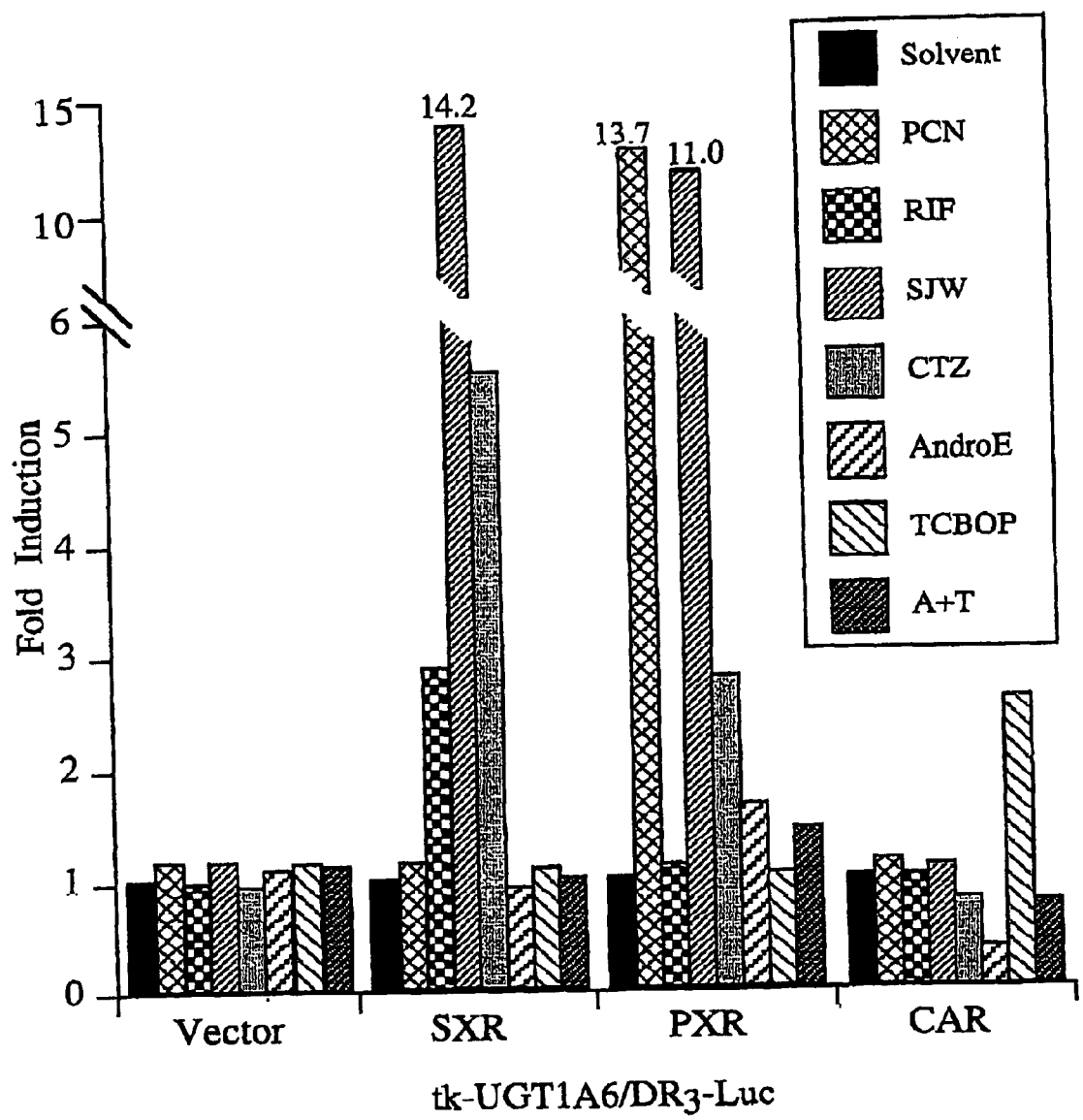
FIG. 2 shows the activation of a UGT reporter gene by SXR, PXR and CAR, in the presence of various test compounds. The reporter gene comprises a thymadine kinase (TK) linked to UGT1A6/DR-3 linked to a luciferace (LUC).

The invention methods are based upon the discovery of aspects of a steroid/xenobiotic clearance pathway, the Phase II pathway, via activation of UGT and the subsequent glucuronidation of steroid and/or xenobiotic compounds. Transfection based assays have been used to determine that SXR/PXR and CAR can promote expression of UGT. In an exemplary assay, a luciferase reporter gene containing the UGT1A6/DR-3 upstream of a minimal thymidine kinase (tk) promoter was constructed and transfected into monkey kidney CV-1 cells together with expression vectors for SXR, PXR, or CAR. Significant activation of the UGT reporter by SXR was seen when RIF, CTZ or extract of St. John's Wort, but not androstanol and TCPOBOP (1,4-bis[2-(3,5-dichloropyridyloxy)] benzene), were added to the culture medium. FIG. 2 illustrates expression of UGT via activation of SXR, PXR, CAR based on the steroid or xenobiotic substance used in the assay. The figure also shows that PXR-mediated UGT activation was seen in the present of St. John's wort, CTZ as well as PCN, which is a PXR-specific ligand. CAR has been shown to activate UGT as well, and is also inhibited or potentiated by the inhibitory ligand androsenol or activating ligand TCPOBOP.

The terms "SXR receptor" and "SXR polypeptide" are interchangeable, the terms "PXR receptor" and "PXR polypeptide" are interchangeable, the terms "CAR receptor" and "CAR polypeptide" are interchangeable, and the terms "UGT", "UGT gene" and "UGT polypeptide" are also interchangeable. These terms, as used herein are intended to include functional fragments of the proteins. Such fragments include peptides having the DNA binding and/or the ligand binding properties of the specific protein (SXR/PXR and/or CAR).

Thus, as shown in FIG. 2 and described above, modulator(s) useful in the practice of the invention method(s) include both agonists and antagonists of SXR/PXR and/or CAR. When the modulator is an agonist, the modulator is characterized as one which activates one of SXR/PXR and/or CAR. Activation of SXR/PXR and/or CAR in turn promotes binding of said receptor to a UGT response element and expression of UGT. Such compounds promote glucuronidation of a therapeutic, endogenous, dietary steroid, dietary lipids, and the like.

In FIG. 2, the tk-UGT1A6/DR3-Luc construct comprises a UGT inverted or direct repeat and/or a nuclear receptor binding site such that activation of the response element results in transcription of UGT. Generally the gene encodes an enzyme effective in metabolism of one or more steroids or xenobiotic substances, such as dietary lipids and phytoestrogens, and also includes a nucleotide sequence that encodes a SXR/PXR and/or CAR response element, for example, one having a direct repeat of a suitable half site (the DR half site) separated by a spacing of 3, 4, or 5 nucleotides, or a direct repeat of a variant thereof. The response element can also comprise an inverse repeat of a suitable half site separated by a 6 nucleotide spacer, or an inverse repeat of a variant thereof, separated by a 6 nucleotide spacer.

Half sites contemplated for use herein have the sequence RGBNNM, wherein:
R is selected from A or G;
B is selected from G, C, or T;
each N is independently selected from A, T, C, or G; and
M is selected from A or C;
with the proviso that at least 4 nucleotides of said—RGBNNM—sequence are identical with the nucleotides at corresponding positions of the sequence AGTTCA.

Examples of response elements suitable for use in practice of the invention methods can be selected from the following:
DR-3,4,5=AGGTCAN$_n$AGGTCA, wherein n is 3, 4, or 5 (SEQ ID NOs:1, 2 and 3);
βDR-3,4,5=AGTTCAN$_n$TGAACT, wherein n is 3, 4 or 5 (SEQ ID NOs: 4, 5 and 6); and
IR-6=TGAACTN$_n$AGGTCA), wherein n is 6 (SEQ ID NO:7), and the like.

Additional inverted repeats include:

```
IR-0,
agcttAGGTCATGACCTa;        (SEQ ID NO: 8)

IR-1,
agcttAGGTCAgTGACCTa;       (SEQ ID NO: 9)

IR-2,
agcttAGGTCAcgTGACCTa;      (SEQ ID NO: 10)

IR-3,
agcttAGGTCAcagTGACCTa,     (SEQ ID NO: 11)

IR-4,
agcttAGGTCAcatgTGACCTa;    (SEQ ID NO: 12)

IR-5,
agcttAGGTCAcactgTGACCTa;   (SEQ ID NO: 13)

IR-6,
agctttTGAACTcaaaggAGGTCA); (SEQ ID NO: 14)
and

IR-M,
agcttACGTCATGACGTa         (SEQ ID NO: 15)
```

Those of skill in the art will recognize that any combination of nucleotides can be used to make up the 3, 4, 5, or 6 nucleotide spacer between the repeated half sites.

Such response elements are generally found in genes encoding catabolic enzymes, such as CYP2A1, CYP2A2, CYP2C1, CYP3A1, CYP3A2, an P450 oxidoreductase, uridine diphosphate glucuronosyltransferase (UGT), or a glucuronosyl transferase, transcription of which genes is activated or suppressed by practice of the invention method(s). Preferably, the present invention response element is part of the UGT gene.

A putative DR-3 type of nuclear receptor binding site has been identified in the rat UGT1A6 gene. FIGS. 1A and 1B illustrate that SXR and CAR bind to a UGT1A6 direct repeat-3. Binding of SXR, VPSXR and VPCAR to UGT is specific to the DR-3 as mutation of the nucleic acids of the DR-3 sequence from those of the UGT1A5/DR-3 results in abrogation of binding. FIGS. 1A and B are the results of electrophoretic mobility shift assays and show data which is consistent with the binding of SXR/RXR or CAR/RXR to the CYP3A23/DR-3.

Representative examples of agonists capable of activating transcription of such catabolic enzymes include molecules that have high-affinity receptors, such as progesterone, testosterone, estrogen and corticosterone, as well as their reduced catabolites that are, for the most part, inactive on the high-affinity receptors. In addition to the natural steroids, the receptors SXR/PXR and CAR are activated by synthetic steroids, including PCN and dexamethasone, as well as by xenobiotic drugs, phytosteroids, and the like. Further agonists include corticosterone, rifampicin, nifedipine, corticosterone, DES, estradiol, dihydrotestosterone, pregnenolone, progesterone, and PCN, with corticosterone being the strongest known activator.

When the modulator is an antagonist of SXR/PXR and/or CAR, the modulator functions in one or more of the following ways: (1) to block binding of the receptor to a UGT response element, (2) to inhibit formation of a heterodimer of the SXR/PXR and/or CAR and a retinoid X receptor, or (3) to inhibit binding of a ligand to the ligand binding domain of SXR/PXR and/or CAR. For example, an antagonist can inhibit formation of a heterodimer between a retinoid X receptor and a SXR/PXR or CAR polypeptide by blocking the docking site between the molecules, or inhibit binding of one of SXR/PXR or CAR to the response element of the UGT gene.

One of skill in the art will be aware of, or can readily devise, additional polypeptides or nucleotides that will act as antagonists of gene transcription in the invention method(s).

Figure 3:
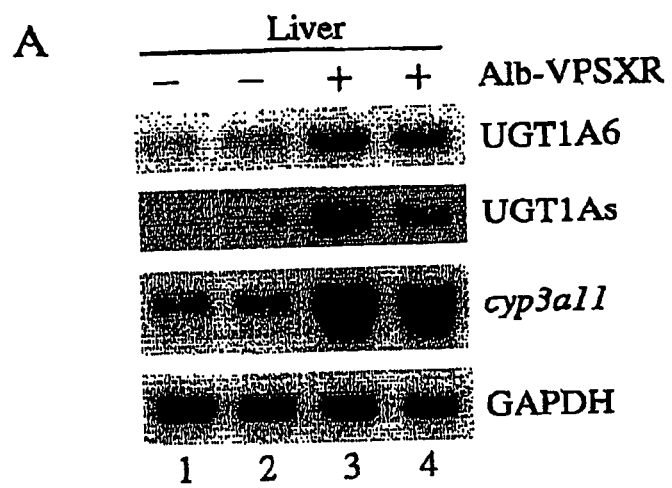
FIG. 3 collectively shows the induction of UGT expression in vivo.
Figure 3:
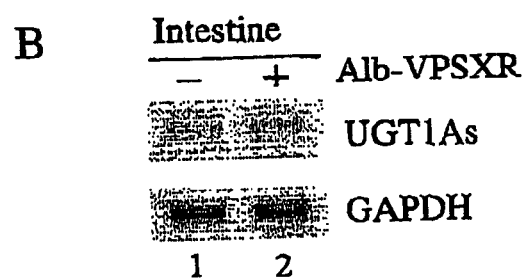
Figure 3:
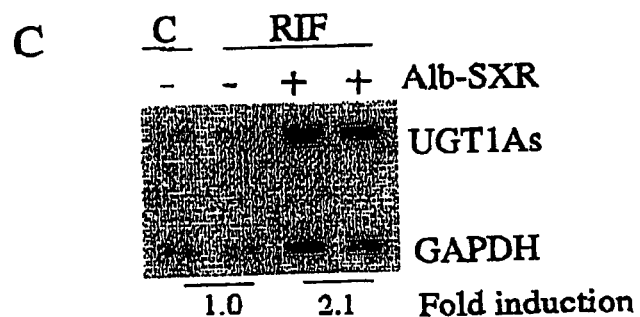
Figure 3:
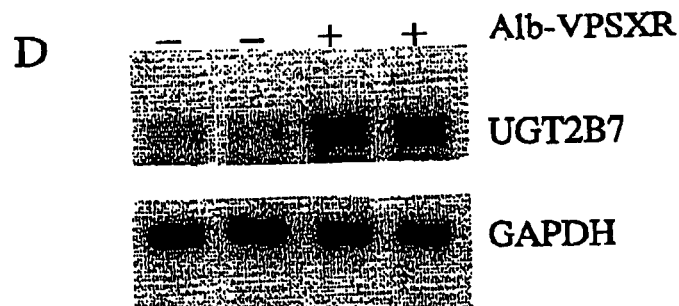

Receptors such as SXR, PXR and/or CAR can bind and activate UGT. FIG. 3 illustrates the results of expression studies of UGT in transgenic mice. In the particular example shown, transgenic mice contain a SXR transgene which is constitutively expressed.

Thus, SXR/PXR and CAR can be transcription regulators for both Phase I and Phase II xenobiotic enzymes and these enzymes are essential for the detoxification and/or clearance of xenobiotics including prescription and non-prescription drugs. The present invention provides a cell culture system as well as transgenic mice such as the Alb-SXR, Alb-VPSXR, PXR null, and PXR null-SXR, transgenic mice for use in invention methods. It is also within the present invention to provide CAR transgenic rodents having inducible CAR and/or constitutive CAR elements as part of the rodent genome. Such rodents can be PXR null, PXR null-SXR, PXR null-CAR, PXR null SXR/CAR, CAR and/or SXR. Such invention mice can be used for methods for screening for the development of drugs with reduced drug-drug interaction potential. One of skill in the art would recognize that having such transgenic mice would allow for in vitro and in vivo assays. FIG. 3 illustrates the results of Northern blot analysis using the first exon of UFGT1A6 as a probe to show that UGT1A6 mRNA is upregulated in the liver of a transgenic mouse (VPSXR mouse with constitutive SXR expression). All of the shared exons of the UGT1A family members were used as probes with similar results. Administering an SXR specific ligand also results in increase expression of UGT1A mRNA. Western Blot analysis of protein content were shown to be consistent with mRNA analysis, illustrating an increase in UGT production as a result of SXR activation. It would be understood by one of ordinary skill in the art that SXR, PXR, and CAR, have been shown to have similar, yet specific, responses and that SXR is provided only as an example and is not a limiting aspect of the present invention.

In an another aspect, the transgenic mice and the cells and tissues of such mice are useful for methods for determining compounds which are Phase I or Phase II xenobiotic enzyme specific. It has been established that the nuclear receptors SXR/PXR and CAR can act as xenosensors to regulate the expression of CYP genes. SXR and PXR have been shown to be mediators of a CYP3A response to xenobiotic compounds as well as activators/mediators of UGT expression and subsequent glucuronidation of steroids or xenobiotic compounds. The present invention provides methods for determining compounds which can activate either Phase I enzymes, for example CYPs, or Phase II enzymes, for example UGTs, or both. Invention methods can comprise assays using cells of transgenic mice or cells that have been transfected with vectors having full or partial SXR/PXR, CAR, CYP or UGT genes either constitutively expressed or under inducible control. Test substances can be assayed to determine which substance activates SXR/PXR and/or CAR and results in the expression/activation of CYP and/or UGT, thereby determining substances that are specific for one pathway or the other.

In a non-limiting example, plasma and urine corticosterone levels have been examined in VPSXR transgenic mice. Both CYP enzymes and UGTs are essential for the metabolism and elimination of steroid hormones. The up-regulation of both Phase I and Phase II xenobiotic enzymes indicate that SXR can promote steroid elimination and up-regulation of the adrenal axis. In the example, mouse plasma and urine samples have been collected and subjected to corticosterone measurement. Unlike humans where the primary glucocorticoid is cortisol, corticosterone is the principal glucocorticoid in rodents. The transgenic VPSXR mice have higher concentrations of corticosterone in both the plasma and urine when compared to wild type animals. The transgenic mouse, having an activated SXR shows increased levels of steroid in both the plasma and the urine which can indicate that SXR can serve as a steroid sensor via activation of CYP and UGT enzymes when the proper substrate is used for activation.

In another aspect the present invention provides a method for screening for drugs with reduced drug-drug interaction potential is provided. Such a method involves a transgenic rodent, such as a mouse for example, wherein the mouse comprises one or more transgenes encoding a xenobiotic nuclear receptor. The method comprises administering test compounds, such as test drugs, to a rodent and screening the hepato-gastrointestinal tissues and/or fluids to ascertain glucuronidation levels. The assay of the invention can also comprise cells or tissues of an invention transgenic mouse, in an in vitro assay, where administration of a test compound or test drug is by addition to the in vitro solution sample.

In another aspect of the present invention, an invention transgenic mouse can be used to evaluate pharmacokinetics in the presence of at least one exogenous xenobiotic nuclear receptor transgene. It would be understood by one of skill in the art that such a method can comprise, for example, measuring clearance and/or glucuronidation of a test drug in mice that have an SXR and/or CAR transgene and have had the native xenobiotic nuclear receptor inactivated, e.g., a PXR null mouse. Such transgenes can be inducible, constitutively expressed and/or operably linked to a reporter construct, containing, for example, a luciferace gene. Substance clearance methods are well known by those of skill in the art and can involve monitoring the release of the test drug via the hepato-gastrointestinal pathways via bile and/or urine. Preferably, clearance of the drug and/or levels of glucuronidation of the drug are monitored in such an assay.

The term "pharmacokinetics" as used herein, refers to the presence and amount of an administered compound at various physiological sites over time following administration. Pharmacokinetics can be evaluated by assessing levels of administered compounds. Methods may include monitoring compound absorption and distribution, chemical modifications of the compound, and storage and elimination of the compound, and the like, as are well known in the art.

In another aspect of the present invention, there are provided transgenic mice and/or mammalian cells comprising a UGT gene as part of one of the cellular genome or as part of an extragenomic vector, in addition to at least one exogenous xenobiotic nuclear receptor transgene. Such transgenic mice and/or cells can be used as part of a method to evaluate the toxicity of a test compound or drug, and for determining the therapeutic index of a test compound or drug. Preferably, such a method has a transgenic mouse or cell having a UGT gene as part of the genome or part of an extragenomic vector. A vector of this particular invention method can comprise an inducible promoter and a reporter, such as thymidine kinase and luciferase, respectively.

The term "therapeutic index" as used herein, is a measure of the approximate safety of an administered drug. A drug with a high index can generally be administered with greater safety than one with a low index. The therapeutic index is ordinarily calculated from data obtained from experiments with animals. It may be calculated as LD50/ED50 in such experiments, or by comparing the ED50 for different effects of the same drug, e.g., detrimental dose to effective dose.

As used herein, detrimental to the health" refers to any difference in health relative to the health of a normal animal.

In accordance with a still further embodiment of the present invention, there are provided probes comprising labeled single-stranded nucleic acid, comprising at least 20 contiguous bases in length having substantially the same sequence as any 20 or more contiguous bases selected from bases of UGT DNA or mRNA sequences, or the complement thereof, for example the first exon of UGT1A6.

As used herein, the term "probe" refers to an oligonucleotide that is complementary to a sequence in a target nucleic acid such that the target nucleic acid can be detected by hybridization as is well known in the art. The probe may be detectably labeled to facilitate identification, detection, and/or localization of the target nucleic acid.

As used herein, nucleotide sequences which are substantially the same share at least about 90% identity, and amino acid sequences which are substantially the same typically share more than 95% amino acid identity. It is recognized, however, that proteins (and DNA or mRNA encoding such proteins) containing less than the above-described level of homology arising as splice variants or that are modified by conservative amino acid substitutions (or substitution of degenerate codons) are contemplated to be within the scope of the present invention. As readily recognized by those of skill in the art, various ways have been devised to align sequences for comparison, e.g., the Blosum 62 scoring matrix, as described by Henikoff and Henikoff, *Proc. Natl. Acad. Sci. USA* 89:10915, 1992. Algorithms conveniently employed for this purpose are widely available (see, for example, Needleman and Wunsch, *J. Mol. Biol.* 48:443, 1970).

Those of skill in the art recognize that probes as described herein can be labeled with a variety of labels, such as for example, radioactive labels, enzymatically active labels, fluorescent labels, and the like.

A presently preferred means to label such probes is with $^{32}$P. Such probes are useful, for example, for determining the levels of UGT mRNA being produced in response to the presence of one or more steroid and/or xenobiotic to regulate the transcription of associated gene(s), said method comprising hybridizing with a probe as described herein under high stringency conditions (e.g., contacting probe and test DNA at 65° C. in 0.5 M NaPO$_4$, pH 7.3, 7% sodium dodecyl sulfate (SDS) and 5% dextran sulfate for 12-24 hours; washing is then carried out at 60° C. in 0.1×SSC, 0.1% SDS for three thirty minute periods, utilizing fresh buffer at the beginning of each wash), and thereafter selecting those sequences which hybridize to said probe.

In yet another aspect of the invention, the above-described probes can be used to assess the tissue sensitivity of an individual to exposure to steroid and steroid-like compounds by determining UGT mRNA levels in a given tissue sample. It is expected that an individual having an elevated level of UGT mRNA (or protein), relative to normal, will have enhanced sensitivity to the presence of significant levels of steroid and xenobiotic compounds, such as are encountered in many foods, or as a result of overproduction and/or reduced ability to degrade steroids, as seen in such diseases as Cushing's syndrome, virilism and hirsutism in females, polycystic ovarian syndrome, and the like.

The term "sensitivity" as used herein refers to the ability of a steroid or steroid-like compound to activate a Phase II pathway. Activation of a Phase II pathway can be determined by assessing UGT activity.

In accordance with yet another embodiment of the present invention, there are provided antibodies which specifically bind the above-described receptor polypeptides. Preferably, such antibodies will be monoclonal antibodies. Those of skill in the art can readily prepare such antibodies having access to the sequence information provided herein regarding invention receptors.

Thus, the above-described antibodies can be prepared employing standard techniques, as are well known to those of skill in the art, using the invention receptor proteins or portions thereof as antigens for antibody production. Both anti-peptide and anti-fusion protein antibodies can be used (see, for example, Bahouth et al., *Trends Pharmacol. Sci.* 12:338-343, 1991; *Current Protocols in Molecular Biology* (Ausubel et al., eds.) John Wiley and Sons, New York, 1989). Factors to consider in selecting portions of the invention receptors for use as immunogen (as either a synthetic peptide or a recombinantly produced bacterial fusion protein) include antigenicity, uniqueness to the particular subtype, and the like.

The availability of such antibodies makes possible the application of the technique of immunohistochemistry to monitor the distribution and expression density of UGT and/or receptors such as SXR/PXR and CAR to the presence of steroids, xenobiotics, drugs and/or test compounds. Such antibodies could also be employed for diagnostic and therapeutic applications.

In accordance with a further aspect of the present invention, there are provided methods of rapidly screening compounds to determine which compounds are putative agonists and/or antagonists of xenobiotic nuclear receptor polypeptides. Such methods comprise determining whether test compounds in the presence of one or more xenobiotic nuclear receptor polypeptides are capable of promoting binding to UGT inverted repeats and/or direct repeats. This method can be used to screen large numbers of compounds rapidly, and is useful for developing compounds which can activate, modulate, or inhibit UGT in a cell. Subsequently, more detailed assays, such as functional assays, can be carried out with initially identified compounds, to further determine whether such compounds act as agonists or antagonists of xenobiotic nuclear receptor polypeptides or UGT.

The term "agonist" as used herein refers to a molecule which binds to a target receptor inducing a change in activity or function of the target receptor. The term "antagonist" as used herein refers to a molecule which attenuates the effect of an agonist.

Invention methods can also be employed to identify new ligands for UGT, by determining whether test compounds promote binding of UGT to UGT inverted repeats and/or direct repeats. Test samples (e.g., biological fluids) may also be subjected to invention assays to determine the glucuronidation levels or absence of glucuronidation of xenobiotics.

Invention methods can also be used to assay of test samples (e.g., biological fluids) for the presence, absence, or relative levels of glucuronidated steroids and/or xenobiotics. Such methods comprise comparing the water solubility of xenobiotics obtained from the samples to the water solubility of non-glucuronidated steroids and/or xenobiotics. Thus, for example, tissue homogenates from a patient displaying symptoms thought to be related to over- or under-production of steroids can be assayed to determine if the observed symptoms are related to the presence of UGT and/or receptors such as SXR/PXR and CAR. With regard to "relative levels" as used herein, it is understood that one of skill in the art would recognize that other pathways and glucuronosyltransferase mechanisms can exist which continue to aid in the glucuronidation of steroids and/or xenobiotic materials for clearance from a subjects body, however the present invention provides methods for assaying levels of UGT activity in relation to administered test compounds, control compounds or potential therapeutics.

As used herein, "water solubility" refers to the amount of the compound dissolved in water or an aqueous medium.

Figure 4A:
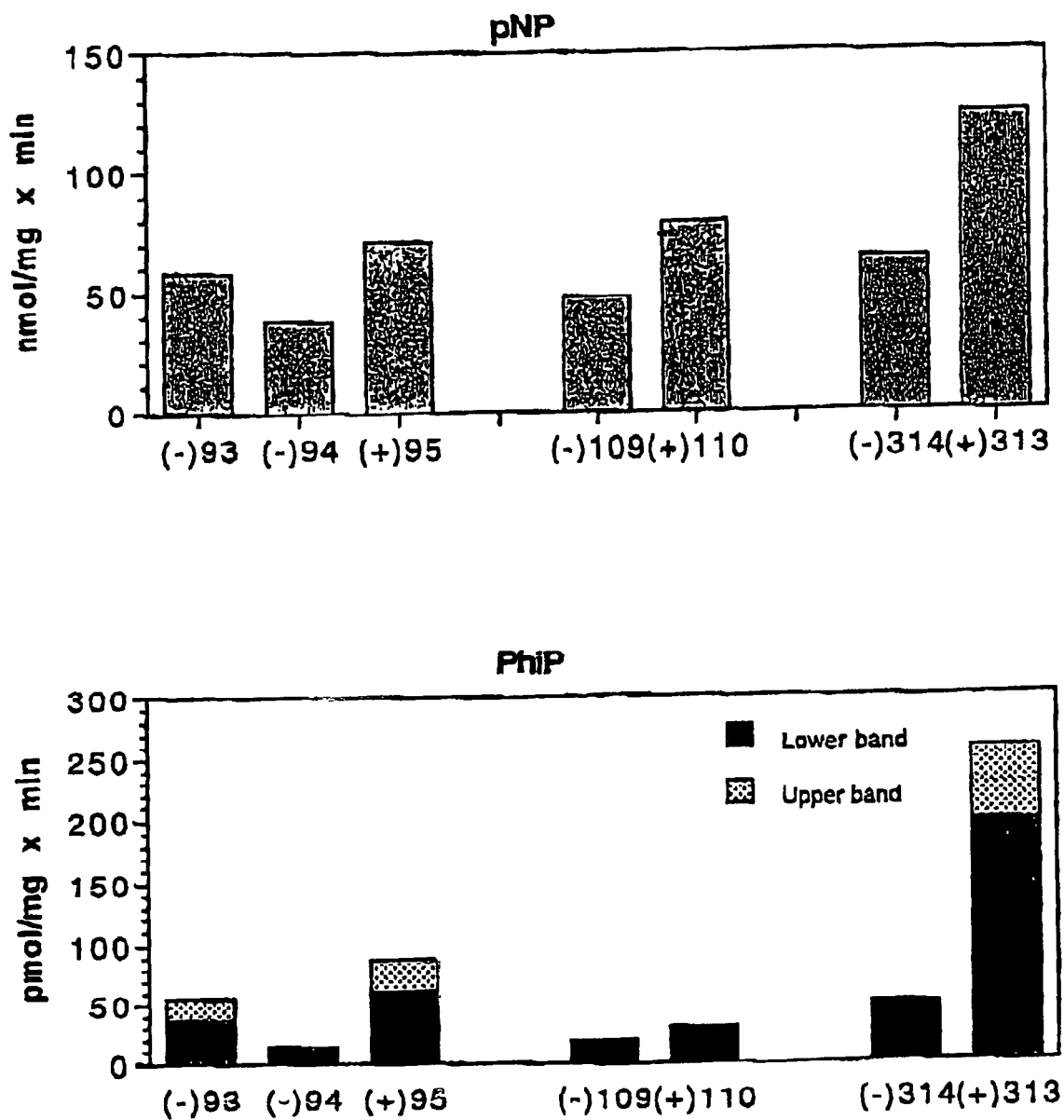
FIG. 4A shows the glucuronidation of pNP and PhiP.
Figure 4B:
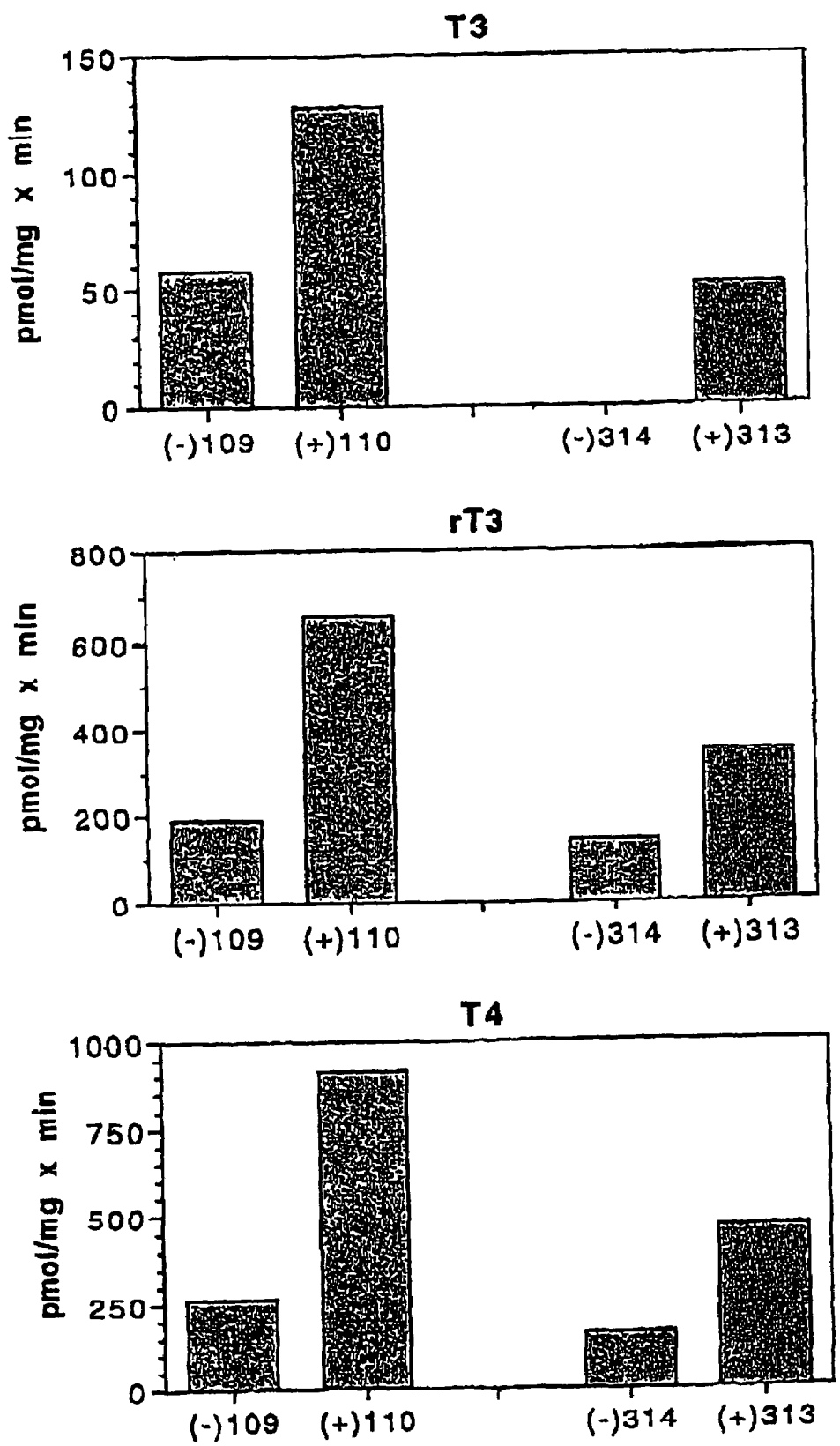
FIG. 4B shows the glucuronidation of and three thyroid hormones (T3, rT3 and T4) in wildtype mice and in transgenic mice.

An example of such an embodiment is the detection of glucuronidated substances in a transgenic mouse (VPSXR). A variety of substances were administered to the mouse, for example, phenols and phenolic corticosteroids, bile acids, retinoids, phenols, oxidized and free fatty acids, and the like. FIG. 4 shows the comparison of the glucuronidation of pNP (poly(N-isopropylacrylamide), a substrate that is actively glucuronidated by UGT1A6 and PhIP, a carcinogen produced in cooked meat and shown to be glucuronidated by at least 4 isoforms from UGT1A subfamily. Liver microsomes have been prepared from the transgenic mouse and shown to exhibit higher UGT activity toward several substrates when compared to wild type liver microsome preparations. In most cases, the substrates were glucuronidated 150%-700% times more in the mice expressing the SXR transgene when compared to wild type mice. Such levels were consistent having values such as 150-500%, 150-160%, 230-400% and 150-250% ranges. Additionally, there was no increase in activity of sulfotransferases with phenolic substrates, indicating the increased enzyme activity is UGT specific. Thus the present invention provides a method for assaying the activity of UGT via the glucuronidation of substrates in a receptor specific manner. It would be understood by one of ordinary skill in the art that SXR, PXR and CAR could be specifically interchanged providing an assay which can be useful in ascertaining the specific ligand reactivity of each receptor in relation to the up-regulation of UGT activity. Moreover, such an assay could be used to ascertain the ability of the xenosensors in upregulating other Phase II detoxification enzymes such as UGTs.

The binding assays contemplated by the present invention can be carried out in a variety of ways, as can readily be identified by one of skill in the art. For example, competitive binding assays can be employed, as well as radioimmunoassays, ELISA, ERMA, and the like.

Optionally, the above-described method of testing can be carried out in the further presence of a ligand for a xenobiotic nuclear receptors, thereby allowing the identification of antagonists thereof. Those of skill in the art can readily carry out antagonist screens using methods well known in the art. Typically, antagonist screens are carried out using a constant amount of agonist, and increasing amounts of a putative antagonist (i.e., a competitive assay). Alternatively, antagonists can be identified by rendering the receptor constitutively active (e.g., by adding a strong, constitutively-active activator to the receptor) and screening for compounds which shut down the resulting constitutively-active receptor.

The identification of UGTs as direct targets for SXR, PXR and CAR has implication in both xenobiotic metabolism and human diseases. UGTs have been implicated in inheritable human diseases, carcinogenesis as well as autoimmunity. For example, mutation in the human UGT1A locus has been linked to inheritable hyperbilirubinemia as a result of decreased glucuronidation and clearance of serum bilirubin. The involvement of UGTs in carcinogenesis was suggested in the Gunn rat, where a mutation in the UGT1A allele renders the entire locus inactive. The production of benxo(a)pyrene glucuronides is dramatically reduced, leading to elevated levels of DNA adducts. Moreover, differential down-regulation of UGT1A mRNA is observed in the early stages of cancer. No such regulation was seen in benign tumorgenesis. As shown herein, environmental mutagens such as amines such as PhIP (2-amino-1-methyl-6-phenylimidazo[4,5-b]pyridine), and benozo(a)pyrenes have been identified as substrates for UGTs.

Thus, it can readily be seen that invention methods can be used to identify a variety of therapeutically useful compounds. The compounds identified as described herein can be used for the treatment of a wide variety of indications, such as, for example:

a) Cushing's syndrome hypercortisolism), which manifests as increased cortisol levels, leading to numerous problems including obesity, fatigue, hypertension, edema and osteoporosis;

b) virilism and hirsutism in females due to overproduction of testosterone;

c) androgen excess due to polycystic ovarian syndrome, which manifests as greatly increased circulating levels of dehydroepiandrosterone;

d) enzymatic defects which lead to accumulation of specific steroids, such as:

1) 21-hydroxylase deficiency leading to increased synthesis of 17-hydroxy-progesterone and androgens;

2) 11β-hydroxylase deficiency leading to deoxycortisol and deoxycorticosterone accumulation and attendant hypertension;

3) 3β-hydroxysteroid dehydrogenase deficiency resulting in accumulation of pregnenolone and dehydroepiandrosterone, leading to sexual ambiguity in both sexes;

4) 17-hydroxylase deficiency, which prevents cortisol synthesis but leads to accumulation of corticosterone and deoxycorticosterone, resulting in hypertension and aberrant development of secondary sexual characteristics in both sexes;

f) ameliorate the effect of substances in the diet and/or environment which act as endocrine disruptors, e.g., estrogens which may be involved in breast, colorectal and prostate cancers (Adlercreutz and Mazur, *Ann. Med.* 29:95-120, 1997); and the like.

Compounds which are specific agonists for SXR without acting as either agonists or antagonists for other steroid receptors will find particular utility where other steroid compounds have been used for their catatoxic properties, while tolerating the negative effects of such therapeutic use (presumably caused by the undesirable activation of previously described steroid receptors, e.g., glucocorticoid receptor). Compounds which are specific agonists for SXR without acting as either agonists or antagonists for other steroid receptors will find particular utility where other steroid compounds have been used for their catatoxic properties, while tolerating the negative effects of such therapeutic use (presumably caused by the undesirable activation of previously described steroid receptors, e.g., glucocorticoid receptor).

In accordance with a still further embodiment of the present invention, there are provided methods for modulating process(es) mediated by invention receptor polypeptides, said methods comprising conducting said process(es) in the presence of at least one agonist, antagonist or antibody raised against invention receptor.

In accordance with yet another embodiment of the present invention, there are provided methods for inducing the expression of steroid degradative enzymes, said method comprising activating SXR/PXR and/or CAR. Exemplary steroid degradative enzymes contemplated for expression herein include steroid hydroxylases, and the like.

In accordance with the present invention, it has further been discovered that induction of some xenobiotic-metabolizing enzymes by pharmacological levels of steroids is regulated by SXR, a class of broad-specificity, low-affinity, nuclear hormone receptors. One benefit of such a receptor-based system is that it induces the expression of xenobiotic metabolizing enzymes only at activator levels sufficiently high to interfere with normal endocrine function. It also makes biological sense that the expression of enzymes with broad substrate specificity, such as cytochrome P450s, can be induced by a receptor responsive to a diverse group of activators, some of which can be substrates for the induced enzymes.

To determine whether the activity of SXR was ligand-dependent, mixtures of natural and synthetic compounds were tested for their ability to activate SXR in transfection-based assays. A mixture containing dehydroepiandrosterone (DHEA) and pregnenolone was observed to be active, suggesting that SXR might be a new steroid receptor. To characterize its response properties, a large variety of steroids, including intermediate and major products of known steroid biosynthetic pathways were tested. Surprisingly, most of these compounds were active, although there were clear differences in potency. Indeed, most of the more than 70 steroids tested showed some activity at high doses. Activation was dependent on the ligand binding domain of SXR since both full-length receptors and GAL4-receptor ligand binding domain chimeras showed similar activity, whereas there was no activation of reporter gene expression in experiments with reporter alone or reporter plus GAL4 DNA-binding domain.

The most potent and efficacious activator of the numerous steroids tested is corticosterone. Estradiol and dihydrotestosterone are also remarkably effective activators while aldosterone and 1,25 dihydroxy vitamin D3 are inactive, even at 50 mM. Although ligands for the classical steroid receptors do show some overlap in receptor specificity, there is no example of a nuclear receptor that can be activated by so many different types of steroids. This broad ligand specificity of SXR parallels that of PPARα, which can be activated by an extremely diverse group of dietary fatty acids at micromolar levels (see, for example, Forman et al., *Proc. Natl. Acad. Sci. USA* 94:4312-4317, 1997; and Gottlicher et al., *Proc. Natl. Acad. Sci. USA* 89:4653-4657, 1992).

The diversity of steroids showing activity on SXR suggests that this novel class of receptors might be able to sense cumulative, as well as individual steroid levels, predicting that combinations of activators might be more active than the individual components. A cocktail containing 10 steroids, each at 10 mM concentration (i.e., an overall steroid concentration of 100 mM), was considerably more active than its individual components at 10 mM, a concentration at which most were inactive. These results confirm that SXR is a broad-specificity, low-affinity, steroid-activated receptor.

An important requirement for physiologic homeostasis is the removal and detoxification of various endogenous hormones and xenobiotic compounds with biological activity. Much of the detoxification is performed by cytochrome P450 enzymes, many of which have broad substrate specificity and are inducible by a bewildering array of compounds, including steroids. The ingestion of dietary steroids and lipids induces the same enzymes and thus, must be integrated into a coordinated metabolic pathway. Instead of possessing hundreds of receptors, one for each inducing compound, the class of receptors described herein indicates the existence of a class of broad-specificity, low-affinity nuclear receptors that monitor total steroid levels and induce the expression of genes encoding xenobiotic metabolizing enzymes. These results indicate the existence of a steroid sensor mechanism for removal of elevated levels of steroids (or steroid-like compounds) from circulation via broad-specificity, low-affinity receptors which represent a novel branch of the nuclear receptor superfamily.

Indeed, a search of the GENBANK database for genes containing putative SXR response elements identified a number of steroid hydroxylases, e.g., CYP2A1, CYP2A2, CYP2C1, CYP2C6, CYP3A1, CYP3A2, P450 oxidoreductase and UDP-glucuronosyltransferase, as candidate target genes. The relevant portions of these sequences are as follows:

```
DR-3
rCYP3A1
tagac AGTTCA tga AGTTCA tctac      (SEQ ID NO: 16)

rCYP3A2
taagc AGTTCA taa AGTTCA tctac      (SEQ ID NO: 17)

rUGT1A6
actgt AGTTCA taa AGTTCA catgg      (SEQ ID NO: 18)

DR-4
rbCYP2C1
caatc AGTTCA acag GGTTCA ccaat     (SEQ ID NO: 19)

rP450R
cac AGGTGA gctg AGGCCA gcagc       (SEQ ID NO: 20)

AGGTCG aaa

DR-5
rCYP2A1
gtgca GGTTCA actgg AGGTCA acatg    (SEQ ID NO: 21)

rCYP2A2
gtgct GGTTCA actgg AGGTCA gtatg    (SEQ ID NO: 22)

rCYP2C6
agtct AGTTCA gtggg GGTTCA gtctt    (SEQ ID NO: 23)

hCYP2E1
gagat GGTTCA aggaa GGGTCA ttaac    (SEQ ID NO: 24)
```

Additional CYP response elements include:

```
CYP3A4,
tagaataTGAACTcaaaggAGGTCAgtgagtgg;  (SEQ ID NO:25)

CYP3A5,
tagaataTGAACTcaaaggAGGTAAgcaaaggg;  (SEQ ID NO: 26)

and

CYP3A7,
tagaataTTAACTcaatggAGGCAgtgagtgg;  (SEQ ID NO: 27)
```

SXR can activate DR-3, DR4 and DR-5 elements that are present in these genes. In a series of transfections, corticosterone along with pregnenolone, progesterone, DHT, estradiol and PCN are consistently among the best activators. Dexamethasone, cortisone and DHEA are in the intermediate group with little response from either aldosterone or cortisol. Consistent with the DNA-binding data, maximal activities are achieved on βDR-3, βDR-4 and βDR-5 elements.

Thus, SXR response elements are found in genes encoding steroid hydroxylases, P450 oxidoreductase, and glucuronosyl transferase. These enzymes can metabolize endogenous as well as xenobiotic compounds and are legitimate targets for a receptor that is activated by pharmacological levels of steroids. SXR is highly expressed in liver, the major expression site of xenobiotic metabolizing enzymes, suggesting that the steroid sensor mechanism is active in the appropriate tissue. In addition, prominent expression is also found in the intestine. Although less is known about the role of this tissue in steroid or xenobiotic metabolism, it is certainly possible that the intestine plays a role in regulating the metabolism of dietary, and perhaps endogenous, steroids. Taken together, these data strongly support the existence of a class of low-affinity, broad-specificity nuclear hormone receptor(s), such as SXR, which function as intracellular "steroid sensor(s)".

The localization of apparent SXR-responsive elements in genes encoding steroid hydroxylases raises the question of whether products of steroid catabolism, such as reduced or hydroxylated corticosterone derivatives, could also activate SXR. Both 5α and 5β reduced forms of corticosterone are effective SXR activators whereas 5α is slightly active and 5β is completely inactive on GR. While a few 5α-reduced steroids remain active (e.g., dihydrotestosterone), virtually all 5β-reduced steroids are unable to activate classical steroid receptors (see Russell and Wilson, *Ann. Rev. Biochem.* 63:25-61, 1994).

Accordingly, the activation of SXR by 5β-reduced steroids reveals a previously unidentified role for these compounds in gene regulation.

6β-hydroxy corticosterone is virtually inactive on SXR and slightly active on GR. CYP3A genes, which contain SXR-activatable response elements, catalyze the hydroxylation of many steroids at the 6 position. Therefore, the inability of 6β-hydroxy-corticosterone to activate SXR suggests that 6-hydroxylation is a potential regulatory step in the SXR signaling pathway.

Thus, in support of the role for members of the SXR class of nuclear receptors proposed herein, it has been demonstrated herein that SXR is activated by an extremely diverse group of steroids and their metabolites, including molecules that have high-affinity receptors such as progesterone, testosterone, estrogen and corticosterone as well as their reduced catabolites that are, for the most part, inactive on the high-affinity receptors. In addition to the natural steroids, SXR is activated by synthetic steroids including PCN and dexamethasone. These data provide a molecular explanation for the paradoxical induction of the CYP3A genes (a.k.a. P450$_{PCN}$) by both glucocorticoid receptor agonists and antagonists since the cyp3A genes harbor a SXR-activatable response element in the promoter region that has been shown to be responsible for PCN and glucocorticoid induction (see Burger et al., supra and Gonzalez et al., supra). Whereas such a result is unexplainable by regulation of traditional, high-affinity steroid receptors, such behavior is consistent with the observed properties of the newly characterized steroid X receptor.

Further tests were conducted to discover whether P450s known to be inducible by PCN and other steroids could be SXR targets. The primary human steroid-inducible P450 is the CYP3A4 gene (Molowa et al., *Proc. Natl. Acad. Sci. USA* 83:5311-5315, 1986; Beaune et al., *Proc. Natl. Acad. Sci. USA* 83:8064-8068, 1986). Unlike the rat and mouse CYP3A genes, all of which contain a DR-3 response element that SXR can activate, the human and rabbit promoters do not contain such an element. Inducibility of CYP3A4 by steroids and xenobiotics has been localized to an 19 base pair element that is functional in transient transfection assays (Barwick et al., *Mol. Pharmacol.* 50:10-16, 1996). This element contains the IR-6 motif (TGAACTcaaaggAGGTCA) (SEQ ID NO:28). Similar elements have been identified in human CYP3A5, and CYP3A7 and in rabbit CYP3A6 genes (Barwick, supra). Tests conducted to determine the ability of SXR to bind a series of inverted repeat elements with spacings from zero to six nucleotides determined that only an IR-6 response element, showed significant binding. As with the direct repeats, these results indicate the binding was dependent on formation of a RXR:SXR heterodimer. In addition, competition binding experiments demonstrated little difference in the apparent affinity of SXR:RXR heterodimers for the βDR4 and CYP3A4 IR-6 response elements. In accord with the known inducibility of the parent promoters, SXR was shown to activate reporter constructs containing the CYP3A4, but not the CYP3A5 or CYP3A7 motifs.

Compounds known to induce CYP3A4 were also shown to activate SXR. The compounds tested included drugs, such as rifampicin and nifedipine; steroid antagonists, such as tamoxifen, spironolactone and PCN; natural and synthetic steroids, such as dexamethasone, diethylstilbestrol, estradiol, dihydrotestosterone, corticosterone and cortisone; and phytoestrogens, such as coumestrol, equol and genistein. Of these compounds, rifampicin, nifedipine, corticosterone, estradiol, DES, and coumestrol were the most potent activators. The mouse receptor PXR responded poorly to these inducers, but was preferentially activated by PCN, a weak activator of SXR PXR is reported to be preferentially activated by pregnanes (21-carbon steroids such as dexamethasone (DEX) and pregnenolone) (Kliewer, supra); however, our tests showed that PXR is similarly activated by 19-carbon androstanes, like testosterone, and 18-carbon estranes, like estradiol. Similar results were obtained with other natural steroids, including progesterone, pregnenolone and dihydroethanoic acid (DHEA).

To demonstrate that the activation of SXR and PXR by high steroid concentrations is not a general property of all steroid receptors, parallel tests were conducted to determine the activation of the human estrogen receptor (ER) by the same panel of compounds. The only endogenous steroids tested that activated the ER were DHT and estradiol. The synthetic ER agonist, DES, and the phytoestrogens, including coumestrol, also activated the human estrogen receptor.

Because the invention SXR-responsive elements are localized in genes encoding steroid hydroxylases, products of steroid catabolism, such as reduced or hydroxylated corticosterone derivatives, were tested for activation of SXR. The results of these tests illustrate that both 5α and 5β reduced forms of corticosterone are effective SXR activators; however, 5α is slightly active, and 5β is completely inactive on GR. While a few 5α-reduced steroids remain active (e.g., dihydrotestosterone), 5β-reduced steroids fail to activate classical steroid receptors Russell and Wilson, supra). Therefore, the activation of SXR by 5β-reduced steroids may reflect a previously undetected regulatory pathway for these compounds. In addition, the virtual inactivity of, 6β-hydroxy corticosterone on SXR, suggests that CYP3A4 catalyzed hydroxylation is a potential definitive regulatory step in steroid metabolism.

These results indicate that the induction of some xenobiotic-metabolizing enzymes by pharmacological levels of steroids, drugs, and xenobiotic compounds is regulated by a broad-specificity sensor, rather than numerous specific receptors. Direct regulation by a broad-specificity sensor, such as the receptors such as SXR, PXR and CAR, is biologically economical since much of the detoxification and catabolism of such compounds is mediated by UGT and the cytochrome P450 family of enzymes, particularly UGT and the CYP3A family, which both metabolize, and are induced by, a wide spectrum of diverse compounds, including steroids.

Based on the above-described studies, a number of relationships have been discovered among target genes, SXR, PXR and CAR, and UGT with regard to regulating cumulative levels of steroids and xenobiotics. Although less is known about the role of gut tissue in steroid metabolism, the gut is known to play an important role in first pass metabolism of dietary, and orally-administered compounds (Holtbecker et al., *Drug Metab. Dispos.* 24:1121-1123, 1996; and Kolars et al., *Lancet* 338:1488-1490, 1991). For example, CYP3A4 is highly expressed in enterocytes (Kolars et al., *J. Clin. Invest.* 90:1871-1878, 1992). Thus, SXR is expressed at high levels in two key tissues for steroid and xenobiotic catabolism. Second, catabolic enzymes expressed in tissues that express SXR are induced by the SXR. SXR response elements have been discovered in the well-characterized CYP3A4 promoter as well as those of P450 oxidoreductase, CYP2A, CYP2C, CYP2E, UGT and glucuronosyl transferase, which are all known to be involved in steroid and xenobiotic catabolism (Gonzalez, *Trends Pharmacol. Sci.* 13:346-352, 1992). Third, compounds known to induce catabolic enzymes activate SXR, PXR and CAR, including drugs (such as rifampicin and nifedipine), steroid receptor agonists and antagonists (such as estrogen and tamoxifen); bioactive dietary compounds (such as phytoestrogens), and the like. In particular, CYP3A4 is known to be inducible (Rendic and Di Carlo, supra) by virtually all the compounds applicants have identified as SXR activators, and the present invention provides evidence that UGT shares activating compounds with SXR, PXR and CAR as well.

One additional member of the new branch of the nuclear receptor superfamily called the steroid and xenobiotic receptor has been discovered in mouse tissue. Screening of a mouse liver cDNA library at reduced stringency resulted in the identification of 39 cDNAs, all of which encoded PXR.1. Orthologous nuclear receptors typically share greater than 90% amino acid identity in the ligand binding domain when comparing rodent and human receptors (e.g., RARα-98% human/mouse (h/m), PPARγ-98% h/m, GR-95% h/m, TRβ-98% h/rat, ERα-89% h/m). Therefore, PXR and SXR may represent α and β subtypes of the steroid and xenobiotic nuclear receptor family. This conclusion is supported by the distinct pharmacological properties of the receptors, as illustrated in the Examples herein. Further screening of mouse and human liver cDNA libraries has failed to identify other family members. It is also possible that PXR and SXR represent unusually divergent orthologous genes. If this were correct, the divergence might reflect adaptation of the receptor to the difference between the diets of rodents and primates and the requirement for the receptor to respond to appropriate food-borne compounds.

The term "effective amount" refers to an amount of compound, the administration of which results in the desired effect. For example, as applied to a SXR, PXR, CAR or UGT polypeptide agonist or antagonist according to the invention, effective amount refers to the amount of compound necessary to modulate metabolism of one or more steroid and/or xenobiotic compounds to a desired level. A desired level means the level effective to treat, cure, or alleviate the symptoms of a disease state for which the therapeutic compound is being administered, or to establish homeostasis, or to reduce the toxicity of a compound. Alternatively, when an agonist according to the invention is employed to prevent steroid toxicity in a subject therapeutically administered one or more therapeutic steroid and/or xenobiotic compounds in treatment of a disease state, the term "effective amount" is an amount necessary to achieve a non-toxic level of steroids and xenobiotic compounds. Toxic and non-toxic levels can be determined by blood tests of the subject being treated for the effects of steroid toxicity. An effective amount of a SXR, PXR, and/or CAR polypeptide antagonist according to the invention used to reduce clearance of a therapeutic steroid or xenobiotic compound is the amount necessary to raise the blood level of the particular therapeutic compound. Since individual subjects may present a wide variation in severity of symptoms and each drug or active agent has its unique therapeutic characteristics, the precise mode of administration, dosage employed and treatment protocol for each subject is left to the discretion of the practitioner.

Amounts effective for the particular therapeutic goal sought will, of course, depend on the severity of the condition being treated, and the weight and general state of the subject. Various general considerations taken into account in determining the "effective amount" are known to those of skill in the art and are described, e.g., in Gilman et al., eds., *Goodman And Gilman's: The Pharmacological Bases of Therapeutics,* 8th ed., Pergamon Press, 1990; and *Remington's Pharmaceutical Sciences,* 17th ed., Mack Publishing Co., Easton, Pa., 1990, each of which is herein incorporated by reference.

Pharmaceutical formulations of the SXR, PXR, and/or CAR polypeptide agonists or antagonists of the present invention can be used in the form of a solid, a solution, an emulsion, a dispersion, a micelle, a liposome, and the like, wherein the resulting formulation contains one or more of the agonists or antagonists contemplated for use in the practice of the present invention, as active ingredients, in admixture with an organic or inorganic carrier or excipient suitable for enteral or parenteral applications. The active ingredients may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. The active compounds (i.e., one or more SXR polypeptide agonist or antagonist) are included in the pharmaceutical formulation in an amount sufficient to produce the desired effect upon the target process, condition or disease.

Pharmaceutical formulations containing the active ingredients contemplated herein may be in a form suitable for oral use, for example, as tablets, troches, lozenges, aqueous or oily suspensions, dispersible powders or granules, emulsions, hard or soft capsules, or syrups or elixirs. Formulations intended for oral use may be prepared according to any method known in the art for the manufacture of pharmaceutical formulations. In addition, such formulations may contain one or more agents selected from a sweetening agent (such as sucrose, lactose, or saccharin), flavoring agents (such as peppermint, oil of wintergreen or cherry), coloring agents and preserving agents, and the like, in order to provide pharmaceutically elegant and palatable preparations. Tablets containing the active ingredients in admixture with non-toxic pharmaceutically acceptable excipients may also be manufactured by known methods. The excipients used may be, for example, (1) inert diluents such as calcium carbonate, lactose, calcium phosphate, sodium phosphate, and the like; (2) granulating and disintegrating agents such as corn starch, potato starch, alginic acid, and the like; (3) binding agents such as gum tragacanth, corn starch, gelatin, acacia, and the like; and (4) lubricating agents such as magnesium stearate, stearic acid, talc, and the like. The tablets may be uncoated or they may be coated by known techniques to delay disintegration and absorption in the gastrointestinal tract, thereby providing sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874, to form osmotic therapeutic tablets for controlled release.

In some cases, formulations for oral use may be in the form of hard gelatin capsules wherein the active ingredients are mixed with an inert solid diluent, for example, calcium carbonate, calcium phosphate, kaolin, or the like. They may also be in the form of soft gelatin capsules wherein the active ingredients are mixed with water or an oil medium, for example, peanut oil, liquid paraffin, or olive oil.

The pharmaceutical formulations may also be in the form of a sterile injectable solution or suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,4-butanediol. Sterile, fixed oils are conventionally employed as a solvent or suspending medium. For this purpose any bland fixed oil may be employed including synthetic mono- or diglycerides, fatty acids including oleic acid), naturally occurring vegetable oils like sesame oil, coconut oil, peanut oil, cottonseed oil, or synthetic fatty vehicles, like ethyl oleate, or the like. Buffers, preservatives, antioxidants, and the like, can be incorporated as required.

Formulations contemplated for use in the practice of the present invention may also be administered in the form of suppositories for rectal administration of the active ingredients. These formulations may be prepared by mixing the active ingredients with a suitable non-irritating excipient, such as cocoa butter, synthetic glyceride esters of polyethylene glycols (which are solid at ordinary temperatures, but liquify and/or dissolve in the rectal cavity to release the active ingredients), and the like.

In accordance with yet another aspect of the invention, there are provided animal models which are useful to study human response to agents for possible up-regulation of GSTs and/or CYP3A. Invention animal models include transgenic non-human animals (e.g. rodents and the like) transformed with nucleic acid encoding human one or more of xenobiotic nuclear receptor, such as SXR, PXR, and/or CAR. Those of skill in the art can readily determine suitable methods for introducing nucleic acid encoding one or more of SXR, PXR, and/or CAR into a suitable host. In another embodiment of the invention, transgenic animal models are provided wherein SXR, PXR, and/or CAR and endogenous homologs thereof have been "knocked out" so as to render the animal model substantially free of any background activity contributed to any homologs thereof. The resulting transgenic animals are referred to herein as "knock-out" animals, based on the protocol whereby sequence encoding SXR, PXR, and/or CAR or homologs thereof is deleted from the genome or such sequence in sufficiently disrupted or inactivated so as to preclude expression of active receptor by the host organism. Those of skill in the art can readily identify numerous methods whereby deletion or inactivation of target sequence (e.g. SXR, PXR, CAR or UGT or homologs thereof) can be accomplished.

Recent important advances have been made in the understanding of the mechanism through which foreign chemicals impact on the P450-dependent metabolic processes. One key discovery is the establishment of potential roles for orphan receptor SXR in mediating the induction of CYP3A family of P450s in response to a variety of xenochemicals including certain drugs and steroids. Electrophoretic mobility shift assays reveal that SXR/RXR heterodimer can bind the IR-6 and DR-3 response elements derived from the promoters of human CYP3A4 genes. Moreover, SXR activates the response element-containing synthetic reporter genes in response to some drug/xenochemicals and steroid hormones, suggesting a potential role of SXR in CYP3A induction. In accordance with the present invention, it is demonstrated that SXR can activate CYP3A cellular promoters in primary rat hepatocyte cultures. Furthermore, introducing the human SXR to produce a transgenic mouse is sufficient to render the mouse liver with a human profile of CYP3A gene inducibility, and expression of an activated form of SXR results in specific and constitutive up-regulation of CYP3A, establishing a central role of SXR/PXR in CYP3A gene induction.

Although there are substantial structural and catalytic similarities among the various members of the CYP3A family across species lines, there are important differences in regulatory control of these genes (for reviews, see Gonzalez, supra, and Nelson, supra). For example, a clear discrepancy between human and rodents is that RIF induces CYP3A4 in human liver (Watkins et al., supra) but does not induce its homologues CYP3A23 in rat (Wrighton et al., supra) and CYP3A11 in mouse (Schuetz et al., supra), respectively. Rifampicin does induce CYP3A6, the homologous form in rabbit (Kocarek et al., supra), yet in the rabbit, PCN, which induces CYP3A23 in rat liver (Wrighton et al., supra), does not induce CYP3A6. PCN is also a poor activator for CYP3A4 (Schuetz et al., supra; Kocarek et al., supra; Blumberg et al., supra; and Lehmann et al., *J. Clin. Invest.* 102: 1016-1023, 1998).

Based on two pieces of evidence, it is proposed that SXR/PXR, rather than the gene structure, determine the inducibility of CYP3A genes: (1) SXR and PXR share similar DNA binding profiles. Steroid and xenobiotic inducibility of human CYP3A4 has been localized to an IR-6 containing 19-bp element (Barwick et al., supra), and a similar element is also present in the rabbit CYP3A6 genes (Barwick et al., supra); whereas the promoters of rodent CYP3A genes contain DR-3 elements. Electrophoretic mobility shift assays reveal that both SXR:RXR and PXR:RXR heterodimers bind to DR-3 and IR-6 elements efficiently (Blumberg et al., supra, and Lehmann et al, supra); (2) When cultured rat hepatocytes were transfected with vectors bearing DR-3 or IR-6-containing 5'-flanking response DNA element from CYP3A23, CYP3A4, or CYP3A6 genes, reporter gene activity was induced on treatment with PCN; whereas RIF treatment had no effect. When the same vectors were transfected into rabbit hepatocytes, increased activity was observed on treatment of the cells with RIF but not with PCN (Barwick et al., supra). However, such trans-species gene transfer has not been tested in the context of the cellular promoters of the CYP genes.

In accordance with the present invention, it is demonstrated that SXR dictates the inducibility of CYP3A in hepatocyte cultures and in transgenic mice, and the DR-3 and IR-6 response elements are interchangeable in the context of rat CYP3A23 cellular promoter. These results provide strong evidence that the host cellular environment, SXR/PXR herein, rather than the structure of the gene dictates the pattern of CYP3A inducibility. Furthermore, a system of trans-species gene transfer and CYP3A inducibility has been established, which could, in turn, provide a unique technique for identifying mechanisms of induction and advancing the development of appropriate toxicological models for human safety assessment.

Thiazolidinediones (TZDs) are a new class of oral antidiabetic agents. They selectively enhance or partially mimic certain actions of insulin, causing a slowly generated antihyperglycaemic effect in Type II (noninsulin dependent) diabetic patients. To date two TZDs, first troglitazone (Rezulin) and more recently Rosiglitazone (BRL49653), have been introduced into clinical use. However, hepatotoxicity, which was anecdotally reported as a problem with ciglitazone and englitazone, has proved to be the main clinical concern with troglitazone (for a review, see Day, *Diabet. Med.* 16:179-192, 1999). In clinical trials, troglitazone-induced hepatotoxicity (alanine aminotransferase level>three times the upper limit of normal) was identified in 1.9% of 2510 patients; these abnormalities resolved with discontinuation of therapy with the drug (for a review, see Watkins and Whitcomb, supra). Indeed, hepatic dysfunction and/or fulminant hepatitis leading to hepatic failure has been reported in patients receiving troglitazone (Neuschwander-Tetri et al., supra, Shibuya et al., supra, and for reviews, see Watkins and Whitcomb, supra, and Day, supra). However, the mechanism of the liver toxicity by TZDs remains largely unknown.

In accordance with the present invention, it has been shown that members of the TZDs selectively activate SXR both in hepatocyte cultures and in transgenic animals. Among the tested TZDs, BRL has the highest binding affinity to PPARγ with a Kd of approximately 40 nM (Lehmann et al., 1995), yet fail to activate SXR; whereas troglitazone and ciglitazone activate SXR. The activation of SXR and subsequent upregulation of CYP3A gene by troglitazone and ciglitazone, together with the fact that constitutive activation of SXR causes liver toxicity, provides a potential mechanism for the known clinical liver toxicity by certain TZDs. However, it remains to be seen whether BRL clinically exhibits reduced or an absence of liver toxicity. Although the VPSXR-induced liver toxicity does not completely mimic troglitazone-induced human liver disease in histological appearance, it is possible that the acute hepatocellular injury present in transgenic mice is a precursor lesion to the confluent necrosis observed in patients with troglitazone injury. The results presented herein also raise the notion that activation of SXR and/or upregulation of CYP3A gene may be applied to screen future TZD drugs and other pharmaceutical compounds. The Alb-SXR transgenic mice, as well as the hepatocyte transfection system, will be invaluable tools in such applications.

The factors responsible for human variation in CYP3A expression are under intense investigation. This variation is believed to influence drug response for up to one-third of all drugs and may also contribute to inter-individual differences in health effects resulting from exposure to CYP3A-metabolized carcinogens in the environment (molars et al., *Pharmacogenetics* 4:247-259, 1994). The extent to which drugs, like RIF, can up-regulate CYP3A is of therapeutic importance because it is co-administered with so many drugs that are CYP3A substrates and thus contributes to increased or decreased effectiveness of these drug therapies as well as adverse side effects (Borcherding et al., *Arch. Intern. Med.* 152:711-716, 1992, and Hebert et al., *Clin. Pharmacol. Ther.* 52:453-457, 1992). However, RIF does not induce CYP3A23 in rat (Wrighton et al., *Mol. Pharmacol.* 28:312-321, 1985) and CYP3A11 in mouse (Schuetz et al., supra), respectively, which in turn limits the application of rodent models in studying RIF-mediated CYP induction.

In accordance with the present invention, Alb-SXR transgenic mice have been successfully generated which are readily responsive to RIF to induce CYP3A gene. The doses of RIF (1-10 mg/kg) that induce CYP3A in these mice are in the range of the standard oral dosing regimen in humans (300-600 mg per 70-kg man). Moreover, the dynamics and the reversibility of RIF-mediated CYP3A induction in the Alb-SXR mice are in agreement with the observation in humans (Kolars et al., 1992), indicating the Alb-SXR mice are indeed an excellent rodent model to study RIF-induced CYP3A response.

The invention will now be described in greater detail by reference to the following non-limiting examples.

EXAMPLE 1

Plasmid Constructs and Mutagenesis

The CYP3A23 cellular promoter reporter, PGL3-CYP3A23, was cloned by inserting the PCR-amplified 5' regulatory sequence of rat CYP3A23 gene (nucleotides-1360 to 82) (Burger et al. 1992) into the PGL3 vector (Promega). PGL3-CYP3A4 contains up to nucleotides-1093 of the 5' flanking regions of the human CYP3A4 gene (Hashimoto et al., 1993). Site-directed mutagenesis was performed by the PCR overextension method (Ho et al., 1989). The PCR-amplified sequences and target mutagenesis were confirmed by DNA sequencing.

The expression vectors for the wild type SXR (pCDG-HX7), an activated form of SXR (pVPG-HX7), and the wild type PXR (pCDG-PXR) were described previously (Blumberg et al, 1998).

EXAMPLE 2

Preparation of Hepatocytes, DNA Transfections and Drug Treatment

Primary cultures of rat hepatocytes were prepared as described previously (Li et al, 1991, and Barwick et al., 1996). Lipofectin (Gibco-BRL)-mediated DNA transfections were carried out as described (Barwick et al., 1996). When necessary, cell were treated with RIF, DEX, PCN, nifedipine, CTZ, corticosterone, coumestrol, RU486, cortisol, 17β-estradiol (E2), pregnenolone, progesterone, cortisone (10 μM each), phenobarbital, 3-methylcholanthrene (3MC) (2 mM each), or the control solvent. All compounds were purchased from Sigma.

EXAMPLE 3

SXR Imparts Trans-species Drug Response of CYP3A Genes to Rat Hepatocyte Cultures A panel of natural and synthetic steroid and nonsteroid compounds were tested for their ability to activate SXR and/or PXR in transfection-based assays using primary rat hepatocytes as recipient cells and the cellular promoters of the rat CYP3A23 gene or the human CYP3A4 gene as reporters. In the absence of SXR, the most potent and efficacious tested activators for CYP3A23 were pregnenolone-16-carbonitrile (PCN), nifedipine, RU486 (another antiglucocorticoid), whereas rifampicin (RIF), clotrimazole (CTZ), phenobarbital, 3-methylcholanthrene (3MC, a known CYP1A2 activator), corticosterone, coumestrol, cortisol, E2, progesterone pregnenolone, and cortisone fail to activate or behave as poor activators. This profile of activation reflects the responsiveness of the endogenous PXR, a rodent homologue of SXR. The failure of RIF to induce rat CYP3A23 gene is consistent with previous observation (Wrighton et al., 1985; and Schuetz et al., 1996). With the co-transfection of SXR, significant induction of CYP3A23 was achieved by RIF, CTZ, phenobarbital, E2, and pregnenolone. The induction of CYP3A23 by nifedipine, and RU486 also increased significantly; while the activation of CYP3A23 by PCN remained unchanged in the presence of SXR. Therefore, transfection of SXR render the responsiveness of rat CYP3A gene by RIF, a known human specific CYP3A activator.

When the human CYP3A4 cellular promoter was used as the reporter, a similar response profile was observed, except that E2 did not induce CYP3A4, and nifedipine did not further potentiate CYP3A4 induction in the presence of SXR. Thus, the human CYP3A4 can be activated by the rodent-specific activator PCN when the promoter was introduced into the rodent cellular environment, presumably via the activation of the endogenous PXR; on the other hand, RIF can active the CYP3A4 in the rodent cellular environment with the introduction of human SXR. The SXR-mediated activation of CYP3A23 or CYP3A4 cellular promoter by RIF exhibited dose dependence of both receptor and ligand.

The fact that SXR is necessary and sufficient to render the induction of both human CYP3A4 and rat CYP3A23 gene in rodent hepatocytes by RIF suggested that the host cellular environment, SXR/PXR herein, rather than the gene structure, dictates the patterns of inducibility of CYP3A genes. The above notion would predict: (1) The SXR/PXR response element is essential for the activation of CYP3A genes; and (2) The response elements of SXR and PXR are interchangeable. Therefore, mutagenesis analysis was performed on the promoter of the rat CYP3A23 gene to examine these predictions. In vitro electrophoretic mobility shift assays showed that both SXR:RXR and PXR:RXR heterodimers efficiently bind to the DR-3 element (5' TGAACTTCATGAACT 3'; SEQ ID NO:29) in the CYP3A23 promoter (Blumberg et al., 1998). Mutation of both half sites (DR3/M1) or a single half site (DR3/M2) abolished the PXR and/or SXR-mediated activation by PCN, RIF, and CTZ. On the other hand, replacement of the wild type DR-3 element by an IR-6 element of the human CYP3A4 gene promoter (Blumberg et al., 1998, and Kliewer et al., 1998) successfully rescue the inducibility by PCN, RIF and CTZ.

Taken together, the transfection results demonstrate that nuclear receptors SXR/PXR are essential in determining patterns of CYP3A inducibility. In addition, these results establish successful development of a cell culture system allowing trans-species gene transfer and CYP3A inducibility.

EXAMPLE 4

Generation and Identification of Transgenic Mice

To generate Alb-SXR and Alb-VPSXR transgenes, the SXR and VPSXR cDNA were released from pCDG-HX7 and pVPG-HX7 (Blumberg et al., 1998), and cloned into the Bam HI site downstream of the mouse albumin promoter/enhancer (Pinkert et al., 1987), respectively. A SV40 intron/poly (A) sequence (Xie et al., 1999) was subsequently placed downstream of SXR and VPSXR cDNAs. The 8.45 kb Alb-SXR, and 8.75 kb Alb-VPSXR transgenes were excised from the vector via Not I and Asp 718 digestion, and purified from agarose gel using QIAquick Gel Extraction Kit (QIAGEN). Microinjection of transgene into one-cell CB6FI mouse zygotes was carried out at the Salk Institute Transgenic Animal Facility. All mice were handled in an accredited Institute facility in accordance with the institutional animal care policies.

Genomic DNA was isolated as described before (Xie et al., 1999). The polymerase chain reaction (PCR) was used to screen the transgene positive mice. Two oligonucleotides used to screen Alb-SXR mice are 5'-GAGCAATTCGCCAT-TACTCTGAAGT-3' (SEQ ID NO:30) (annealing to SXR cDNA), and 5'-GTCCTTGGGGTCTTCTACCTTTCTC-3' (SEQ ID NO:31) (annealing to the SV40 sequence downstream of the transgene in the transgene cassette). Another two oligonucleotides used to screen Alb-VPSXR are 5'-GAC-GATTTGGATCTGGACATGTTGG-3' (SEQ ID NO:32) (annealing to VP16 sequences), and 5'-GTTTTCATCT-GAGCGTCCATCAGCT-3' (SEQ ID NO:33) (annealing to the SXR cDNA). PCR was carried out in a DNA thermal cycler (Perkin-Elmer/Cetus) using the following program: 94° C. for 1 min, 58° C. for 2 min, and 72° C. for 3 min and products were analyzed by electrophoresis on a 1% agarose gel. The transgene integration status was analyzed by Southern blot using transgene specific probes as described before (Xie et al., 1999).

EXAMPLE 5

Generation of Alb-SXR and Alb-VPSXR Transgenic Mice

Transgenic mice expressing wild-type or an activated form of SXR under the control of the liver-specific promoter/enhancer for the mouse albumin gene (Pinkert et al., 1987) were generated by injection of one-cell CB6F I mouse zygotes with the transgene. This promoter fragment has been shown to direct faithfully the expression of the transgene in the liver of transgenic mice (Pinkert et al., 1987). The activated form of SXR (VPSXR) was generated by fusing the VP16 activation domain of the herpes simplex virus to the amino-terminal of SXR. Transfection of VPSXR expression vector into rat hepatocytes resulted in constitutive upregulation of the CYP3A23 gene. Transgene-positive founders were identified by PCR using a pair of transgene-specific oligonucleotides, and the integrity of both transgenes was confirmed by Southern blot analysis. A total of two and seven gene-positive founders were obtained for Alb-SXR and Alb-VPSXR transgene, respectively.

The expression of transgenes was assessed by Northern blot analysis of RNA from the mouse livers using a transgene-specific probe. Thus, twenty microgram of liver total RNAs were subjected to Northern blot analysis. The membranes were hybridized with [$^{32}$P]-labeled 3 kb SXR-SV40 DNA fragment from the transgene. The filters were subsequently stripped and re-probed with PXR cDNA probe, and the glyceraldehyde-3-phosphate dehydrogenase (GAPDH) cDNA for the purpose of loading control. The transgene transcripts (2.6 kb and 2.9 kb for Alb-SXR and Alb-VPSXR transgene, respectively) were detected in the liver of Alb-SXR, and Alb-VPSXR transgenics, but not in a non-transgenic control animal. The expression of endogenous PXR remains unchanged in the transgenic mice.

Initial Northern blotting revealed that Alb-SXR line 2198, and Alb-VPSXR lines 2224 and 2218 ad relatively high expression of the transgenes, and were characterized further. The expression of Alb-SXR (2.6 kb) or Alb-VPSXR (2.9 kb) transgene was specifically detected in the livers of transgenic mice but not in their non-transgenic littermates. Furthermore, the expression of SXR transgenes did not alter the expression of endogenous PXR. No transgene expression was seen in the small intestine, brain and kidney, consistent with the tissue-specificity of the albumin promoter (Pinkert et al., 1987).

EXAMPLE 6

Drug Responsiveness of CYP3A in SXR Transgenic Mice

The animals were allowed free access to food and water at all times. RIF (1-10 mg/kg when necessary), BRL (20 mg/kg, a gift from Dr. Richard Heyman of Ligand Pharmaceutical), ciglitazone (150 mg/kg, Biomol), and troglitazone (150 mg/kg) were administered via gastric lavage. When necessary, mice were treated with a single intraperitoneal injection of DEX (50 mg/kg), PCN (40 mg/kg), or CTZ (50 mg/kg).

To examine the drug response of the endogenous liver CYP3A11 gene, animals were treated with single dose of compounds 24 h before sacrifice, and the CYP3A11 gene expression was evaluated by Northern blot analysis on liver total RNA. Total RNA was prepared from tissues using the TRIZOL Reagent (Gibco-BRL). RNA was separated on 1.25% agarose-6% formaldehyde gel and transferred to a Nytran membrane (Schleicher & Schuell). To detect specific transcripts, [$^{32}$P]-cDNA probes labeled by Random Primer Labeling Kit (Boringher) were hybridized to the membranes. The probe used to detect transgene contains both the SXR cDNA and the SV40 sequences. The PXR cDNA probe was as described previously (Blumberg, et al. 1998). The probes of CYP3A11 gene (nucleotides 1065 to 1569) (Yanagimoto et al. 1992), CYP7A (nt 973 to 1453) (Jelinek et al., 1990), CYP1A2 (nucleotides 1151 to 1565) (Kimura et al., 1984) were cloned by RT-PCR using mRNA from wild type mouse liver. The filters were subsequently stripped and rehybridized with a murine glyceraldehyde-3-phosphate dehydrogenase (GAPDH) cDNA probe for RNA loading normalization.

As observed by Northern blot analysis, RIF (5 mg/kg body weight) specifically induced the expression of CYP3A11 in transgenic mice but not in their wild type littermates. Alb-SXR transgenic mice or control non-transgenic animals were treated with a single dose of RIF (5 mg/kg, gastric lavage), CTZ or PCN (50 mg/kg and 40 mg/kg, respectively, intraperitoneal injection). Tissues were harvested 24 h later and subjected to Northern blot analysis. Membranes were probed with CYP3A11 cDNA probe, and were subsequently stripped and re-probed with GAPDH and transgene specific probes. The increased expression of CYP3A11 in transgenics in response to RIF is of particular note.

The inability of RIF to induce CYP3A11 in wild type mice at this dose is consistent with previous observations (Schuetz et al., 1996). In agreement with transfection results, CTZ caused a moderate level, and a higher level of CYP3A11 induction in wild type animals and Alb-SXR mice, respectively; PCN is an equally efficacious CYP3A11 inducer in both wild type and transgenic animals. The induction of CYP3A11 in Alb-SXR mice is ligand dependent, as no CYP3A11 induction was observed in the absence of an inducer, and the level of transgene expression remained unchanged upon CYP3A11 gene activation.

Dynamics and dose-response of RIF treatment was investigated in Alb-SXR transgenic mice. In the study of dynamics, mice were subjected to daily treatment of RIF for the indicated period of time, and tissues were harvested 24 h after the last treatment. In the study of dose-response, mice were treated with a single dose of indicated amounts of RIF 24 h before tissue harvest. The reduction of RIF-induced expression of CYP3A11 by five days of RIF withdrawal after an initial 7-day treatment is significant. The CYP3A11 induction by RIF is rapid, and a significant induction was achieved after 12 h of RIF administration, with a plateau achieved by 24 h in the continuous presence of RIF. No CYP3A11 induction was observed in non-transgenic mice even after 7 d of RIF administration. Moreover, the RIF-induced expression of CYP3A11 was reversible, significant reduction of CYP3A11 expression was seen by five days of RIF withdrawal after an initial 7-day treatment. The RIF-mediated CYP3A11 induction is also dose-dependent, increased hepatic CYP3A11 mRNA was seen with as little as 1 mg/kg of RIF administration, and the induction was further enhanced with increasing does of RIF, plateauing around 3-5 mg/kg. The dynamics and the reversibility of CYP3A induction by RIF is in agreement with the observation in humans (Kolars et al., 1992).

The CYP3A11 gene is constitutively induced in the livers of Alb-VPSXR transgenic mice, and its expression was not further enhanced by RIF treatment. Of note, the upregulation of CYP gene is liver- and CYP3A11-specific, as: (1) the expression of CYP3A11 in the small intestine remains unchanged, (2) the expression of liver CYP7A gene (cholesterol 7α-hydroxylase), as well as the liver-specific CYP1A2 gene, remains unchanged in the Alb-VPSXR mice. CYP7A is a key enzyme of bile acid biosynthesis, and a responsive gene of FXR (Forman et al., 1995; Wang et al.; 1999, Park et al.; 1999; and Makishima et al., 1999).

EXAMPLE 7

Histologic Evaluation, BrdU Labeling and Immunohistochemistry

Gross and microscopic evaluation were performed. Tissues were fixed in 4% formaldehyde in 1×PBS, embedded in paraffin, sectioned at 5 μm. Hematoxylin and eosin stains, or the Gomori's trichrome stains were performed for histological examination. In vivo BrdU labeling was performed by intraperitoneal injection of BrdU (Sigma) as described (Xie et al., 1998). The sections were immunostained with a rat monoclonal anti-BrdU antibody MSA250P (1:200) (Accurate) using Vectastain Elite ABC Kit (Vector). The chromogen is 3,3'-diaminobenzidine tetrahydrochloride (DAB), and sections were counterstained with Gill's Hematoxylin (Vector).

While the invention has been described and exemplified in sufficient detail for those skilled in this art to make and use it, various alternatives, modifications, and improvements should be apparent without departing from the spirit and scope of the invention. The present invention is well adapted to carry out the objects and obtain the ends and advantages mentioned, as well as those inherent therein. The examples provided here are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

The disclosure of all publications cited above are expressly incorporated herein by reference, each in its entirety, to the same extent as if each were incorporated by reference individually.

That which is claimed is:

1. An assay for determining whether one or more test compound(s) activate UDP-glucuronosyl transferase (UGT) glucuronidation, said assay comprising:

contacting a mammalian kidney host cell containing a xenobiotic nuclear receptor polypeptide and a reporter construct under control of a UGT response element with one or more test compound(s) in an appropriate culture medium, and determining whether test compound(s) promote(s) expression of the reporter, thereby determining whether said test compound activates UGT glucuronidation, wherein said xenobiotic nuclear receptor polypeptide is selected from the group consisting of SXR, PXR, and CAR, wherein said reporter construct comprises:
(a) a promoter that is operable in said host cell,
(b) a UGT1A6/DR-3 response element,
(c) a DNA encoding a reporter protein,
wherein said DNA is operatively linked to said promoter for transcription of said DNA, and
wherein said promoter is operatively linked to said UGT response element for activation thereof.

2. An assay according to claim 1, wherein said promoter is selected from the group consisting of CYP3A23 and CYP3A4 genes for use in said reporter construct.

3. An assay according to claim 1, wherein component (c) of said reporter construct is a luciferase gene.

4. An assay according to claim 1 wherein said response element comprises the sequence of SEQ ID NO:18.

* * * * *

```
                        SEQUENCE LISTING

<160> NUMBER OF SEQ ID NOS: 34

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(9)
<223> OTHER INFORMATION: a, t, c or g

<400> SEQUENCE: 1
aggtcannna ggtca                                                          15

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(10)
<223> OTHER INFORMATION: a, t, c or g

<400> SEQUENCE: 2
aggtcannnn aggtca                                                         16

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, t, c or g

<400> SEQUENCE: 3
aggtcannnn naggtca                                                        17

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(9)
<223> OTHER INFORMATION: a, t, c or g
```

```
<400> SEQUENCE: 4
agttcannnt gaact                                                15

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(10)
<223> OTHER INFORMATION: a, t, c or g

<400> SEQUENCE: 5
agttcannnn tgaact                                               16

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, t, c or g

<400> SEQUENCE: 6
agttcannnn ntgaact                                              17

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, t, c or g

<400> SEQUENCE: 7
tgaactnnnn nnaggtca                                             18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
agcttaggtc atgaccta                                             18

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 9
agcttaggtc agtgaccta                                                    19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
agcttaggtc acgtgaccta                                                   20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
agcttaggtc acagtgacct a                                                 21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
agcttaggtc acatgtgacc ta                                                22

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
agcttaggtc acactgtgac cta                                               23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
agctttgaac tcaaaggagg tca                                               23

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 15
agcttacgtc atgacgta                                                18

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tagacagttc atgaagttca tctac                                        25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
taagcagttc ataaagttca tctac                                        25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
actgtagttc ataaagttca catgg                                        25

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
caatcagttc aacagggttc accaat                                       26

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cacaggtgag ctgaggccag cagcaggtcg aaa                               33

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 21
gtgcaggttc aactggaggt caacatg 27

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gtgctggttc aactggaggt cagtatg 27

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
agtctagttc agtgggggtt cagtctt 27

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gagatggttc aaggaagggt cattaac 27

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tagaatatga actcaaagga ggtcagtgag tgg 33

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tagaatatga actcaaagga ggtaagcaaa ggg 33

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 27
tagaatatta actcaatgga ggcagtgagt gg                                    32

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tgaactcaaa ggaggtca                                                    18

<210> SEQ ID NO 29
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tgaacttcat gaact                                                       15

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gagcaattcg ccattactct gaagt                                            25

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gtccttgggg tcttctacct ttctc                                            25

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gacgatttgg atctggacat gttgg                                            25

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 33
gttttcatct gagcgtccat cagct                                              25

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
actgtagaac ataaagaaca catgg                                              25
```